United States Patent
Conrad

(10) Patent No.: US 11,879,889 B2
(45) Date of Patent: Jan. 23, 2024

(54) RESPIRATORY TESTING WITH MULTIPLE SPECTROMETERS

(71) Applicant: Omachron Intellectual Property Inc., Hampton (CA)

(72) Inventor: Wayne Ernest Conrad, Hampton (CA)

(73) Assignee: Omachron Intellectual Property Inc., Hampton (CA)

( * ) Notice: Subject to any disclaimer, the term of this patent is extended or adjusted under 35 U.S.C. 154(b) by 579 days.

(21) Appl. No.: 16/866,271

(22) Filed: May 4, 2020

(65) Prior Publication Data

US 2021/0341460 A1 Nov. 4, 2021

(51) Int. Cl.
*G01N 33/497* (2006.01)
*G01N 15/14* (2006.01)

(52) U.S. Cl.
CPC ........... *G01N 33/497* (2013.01); *G01N 15/14* (2013.01); *G01N 2033/4975* (2013.01)

(58) Field of Classification Search
CPC ............. G01N 33/497; G01N 2033/4975
See application file for complete search history.

(56) References Cited

U.S. PATENT DOCUMENTS

| | | | | |
|---|---|---|---|---|
| 6,599,253 B1* | 7/2003 | Baum | ............... | G01N 33/497 356/303 |
| 2011/0261366 A1* | 10/2011 | Tearney | ............... | G02B 6/32 356/479 |
| 2015/0226128 A1* | 8/2015 | Byrd | ............... | F02C 7/25 454/252 |
| 2019/0041321 A1* | 2/2019 | Linden | ............... | G01N 21/35 |
| 2021/0131921 A1* | 5/2021 | Roine | ............... | B03C 3/41 |

* cited by examiner

*Primary Examiner* — Nathaniel J Kolb
(74) *Attorney, Agent, or Firm* — Philip C. Mendes da Costa; BERESKIN & PARR LLP/S.E.N.C.R.L., s.r.l.

(57) ABSTRACT

A test method for testing for presence of a biological agent, a test apparatus and a system to control entry to an event uses particle count and spectrographic data. The present embodiments of the invention provide testing apparatuses, systems and methods. These embodiments may provide for an apparatus, system and method for non-invasive respiratory testing with multiple spectrometers. Also, the embodiments may provide for a system and method for determining test sufficiency for a non-invasive respiratory testing apparatus. Also, the embodiments may provide for a system and method for permitting access to a venue for a subject.

7 Claims, 15 Drawing Sheets

RESPIRATORY TESTING WITH MULTIPLE SPECTROMETERS

FIELD

The described embodiments relate to apparatuses, systems and methods for non-invasive respiratory disease testing, and specifically towards the non-invasive testing of subjects having Coronavirus disease 2019 (COVID-19).

BACKGROUND

The term "coronavirus" refers to a large group of viruses known to affect birds and mammals, including humans.

Coronavirus disease 2019 (COVID-19) is an infectious disease caused by severe acute respiratory syndrome coronavirus 2 (SARS-CoV-2). The disease was first identified in December 2019 in Wuhan, the capital of China's Hubei province and spread globally, resulting in the ongoing 2019-20 coronavirus pandemic.

Common symptoms of COVID-19 include fever, cough, and shortness of breath. Other symptoms may include fatigue, muscle pain, diarrhea, sore throat, loss of smell, and abdominal pain. The time from exposure to onset of symptoms is typically around five days but may be much longer including from two to fourteen days. A significant problem affecting the pandemic response to COVID-19 is that asymptomatic carriers can transmit the disease long before the carrier experiences symptoms. While COVID-19 is most contagious during the first three days after the onset of symptoms, the spread is possible before symptoms appear and in later stages of the disease. While the majority of cases result in mild symptoms, some have serious complications requiring hospitalization and potentially causing death.

The virus is spread primarily between humans during close contact, including via small droplets produced by coughing, sneezing, or talking. While these droplets are produced when breathing out, they generally fall to the ground or onto surfaces rather than being infectious over long distances. People may also become infected by touching a contaminated surface and then touching their eyes, nose, or mouth. The virus can survive on surfaces up to 72 hours.

Conventional testing for COVID-19 includes via a real-time reverse transcription polymerase chain reaction (rRT-PCR) from a nasopharyngeal swab. Chest CT imaging may also be helpful for diagnosis in individuals where there is a high suspicion of infection based on symptoms and risk factors. These invasive tests require medical reagents, trained medical staff, and a substantial amount of time in order to provide a test result.

Therefore, there is a need for a non-invasive test for COVID-19 that addresses these needs.

SUMMARY

The present embodiments provide testing apparatuses, systems and methods. These embodiments may provide for an apparatus, system and method for non-invasive respiratory testing. Also, the embodiments may provide for a system and method for determining test sufficiency for a non-invasive respiratory testing apparatus. Also, the embodiments may provide for a system and method for permitting access to a venue for a subject.

In a first aspect, there is provided a non-invasive respiratory test apparatus for a subject which uses spectroscopy to determine the presence of a biological agent such as a virus (e.g., COVID 19). Optionally, the apparatus includes a particle detector to determine if a sufficient sample has been obtained from a subject. The particle detector may determine the particle count and/or particle size range of particles in an exhalation of the subject. In accordance with this aspect, there is provided an apparatus comprising: a casing comprising a first opening for receiving a breath sample of the subject, the casing and the first opening defining a chamber; one or more particle detector portions located within the chamber; one or more spectrometer portions located within the chamber; and a processor portion connected to the one or more particle detector portions and the one or more spectrometer portions.

In one or more embodiments, the casing may have a tapered shape, the tapered shape may comprise a first portion proximate to the first opening having a larger diameter than a second portal distal from the first opening.

In one or more embodiments, the apparatus may further comprise: one or more intake members; the one or more intake members and the casing defining an air flow entry port; the air flow entry port receiving an air flow and creating a boundary layer proximate to an inside of the casing.

In one or more embodiments, the apparatus may further comprise: a fan system; wherein the air flow entry port receives the air flow from the fan system.

In one or more embodiments, the apparatus may further comprise: a drying system; wherein the fan system receives the air flow from the drying system.

In one or more embodiments, the drying system may be one of the group of a refrigeration system and a desiccant system.

In one or more embodiments, the apparatus may further comprise: an air filter system; and wherein the fan system receives the air flow from the filter system.

In one or more embodiments, the air filter system may be a HEPA® filter system.

In one or more embodiments, the apparatus may further comprise: one or more cyclone systems; and wherein the air filter system may receive the air flow from the one or more cyclone systems.

In one or more embodiments, the apparatus may further comprise: a wiper connected to the casing the wiper comprising a cleaning system for cleaning the casing; and the wiper moveable relative to the casing.

In one or more embodiments, the casing may be made from an antiviral substance.

In one or more embodiments, the antiviral substance may be one or more of copper, zinc, and silver.

In one or more embodiments, the casing may be a tapered cylinder.

In one or more embodiments, the apparatus may further comprise: an Ultraviolet (UV) cleaning portion located within the casing.

In a second aspect, there is provided a method for determining a sample sufficiency for non-invasive respiratory testing of a subject, the method comprising: receiving, at an opening of a chamber, a breath sample from the subject; receiving, at a processor from one or more particle detectors in the chamber, particle size data and particle count data from the breath sample; determining, at the processor, a particle size result based on whether the particle size data falls within a particle size threshold; determining, at the processor, a particle count result based on whether the particle count data falls within a particle count threshold; and displaying, at a user interface in communication with the processor, an indication of sample sufficiency based on the particle size result and the particle count result.

In one or more embodiments, optionally if the indication of sample sufficiency indicates an insufficient sample state, displaying, at the user interface, an indication for the user to contribute an additional sample.

In one or more embodiments, the particle size data and particle count data may be received from two or more particle detectors in the chamber.

In one or more embodiments, the method may further comprise: receiving, at the processor from a proximity detector, subject distance data; determining, at the processor, a subject distance result based on whether the subject distance falls within a subject distance threshold; and wherein the indication of sample sufficiency may further comprise an indication for the user to move closer and contribute an additional sample.

In one or more embodiments the proximity detector may be a light curtain.

In a third aspect, there is provided a system for determining a sample sufficiency for non-invasive respiratory testing of a subject that implements the method for determining a sample sufficiency for non-invasive respiratory testing of one or more embodiments.

In a fourth aspect, there is provided a method for non-invasive respiratory testing of a subject, the method comprising: receiving, at an opening of a chamber, a breath sample from the subject; receiving, at a processor, first spectrum data of the breath sample from a first spectrometer; determining, at the processor, a testing indication based on the first spectrum data of the breath sample; outputting, at a display device, the testing indication.

In one or more embodiments, the method further comprises: receiving, at the processor, second spectrum data from a second spectrometer; receiving, at the processor, third spectrum data from a third spectrometer; wherein the testing indication is determined based on the first spectrum data, the second spectrum data, and the third spectrum data.

In one or more embodiments, the determining, at the processor, a testing indication may further comprise performing sensor fusion on the first spectrum data, the second spectrum data, and the third spectrum data.

In one or more embodiments, the determining, at the processor, a testing indication may further comprise: determining a first spectrometer indication based on the first spectrum data; determining a second spectrometer indication based on the second spectrum data; determining a third spectrometer indication based on the third spectrum data; determining the testing indication by performing an arbitration of the first spectrometer indication, the second spectrometer indication, and the third spectrometer indication.

In one or more embodiments, the determining, at the processor, a testing indication may further comprise: receiving, at the processor, fourth spectrum data from a fourth spectrometer; receiving, at the processor, fifth spectrum data from a fifth spectrometer; determining a fourth spectrometer indication based on the fourth spectrum data; determining a fifth spectrometer indication based on the fifth spectrum data; determining the testing indication by performing an arbitration of the first spectrometer indication, the second spectrometer indication, the third spectrometer indication, the fourth spectrometer indication, and the fifth spectrometer indication.

In one or more embodiments, the determining, at the processor, a testing indication may further comprise: receiving, at the processor, sixth spectrum data from a sixth spectrometer; receiving, at the processor, seventh spectrum data from a seventh spectrometer; determining a sixth spectrometer indication based on the sixth spectrum data; determining a seventh spectrometer indication based on the seventh spectrum data; determining the testing indication by performing an arbitration of the first spectrometer indication, the second spectrometer indication, the third spectrometer indication, the fourth spectrometer indication, the fifth spectrometer indication, the sixth spectrometer indication, and the seventh spectrometer indication.

In one or more embodiments, the determining, at the processor, a testing indication may further comprise: receiving, at the processor, eighth spectrum data from an eighth spectrometer; receiving, at the processor, ninth spectrum data from a ninth spectrometer; determining an eighth spectrometer indication based on the eighth spectrum data; determining a ninth spectrometer indication based on the ninth spectrum data; determining the testing indication by performing an arbitration of the first spectrometer indication, the second spectrometer indication, the third spectrometer indication, the fourth spectrometer indication, the fifth spectrometer indication, the sixth spectrometer indication, the seventh spectrometer indication, the eighth spectrometer indication, and the ninth spectrometer indication.

In a fifth aspect, there is provided a system for non-invasive respiratory testing of a subject, the system comprising: a chamber, the chamber comprising: an opening for receiving a breath sample from the subject; and a first spectrometer for collecting first spectrum data of the breath sample, a memory; and a display device for displaying a testing indication, a processor in communication with the first spectrometer, the memory, and the display device, the processor configured to: receive the first spectrum data of the breath sample from the first spectrometer; determine the testing indication based on the first spectrum data of the breath sample; output, at the display device, the testing indication.

In one or more embodiments, the system may further comprise: the chamber may further comprise a second spectrometer for collecting second spectrum data of the breath sample and a third spectrometer for collecting third spectrum data of the breath sample; the processor may be further configured to: receive the second spectrum data from the second spectrometer; and receive the third spectrum data from the third spectrometer, wherein the testing indication may be determined based on the first spectrum data, the second spectrum data, and the third spectrum data.

In one or more embodiments, the determining, at the processor, a testing indication may further comprise performing sensor fusion on the first spectrum data, the second spectrum data, and the third spectrum data.

In one or more embodiments, the processor may be further configured to determine the test indication by: determining a first spectrometer indication based on the first spectrum data; determining a second spectrometer indication based on the second spectrum data; determining a third spectrometer indication based on the third spectrum data; determining the testing indication by performing an arbitration of the first spectrometer indication, the second spectrometer indication, and the third spectrometer indication.

In one or more embodiments, the system may further comprise: the chamber may further comprise a fourth spectrometer for collecting fourth spectrum data of the breath sample and a fifth spectrometer for collecting fifth spectrum data of the breath sample; wherein the processor may be further configured to determine the test indication by: receiving fourth spectrum data from the fourth spectrometer; receiving fifth spectrum data from the fifth spectrometer; determining a fourth spectrometer indication based on the fourth spectrum data; determining a fifth spectrometer indication based on the fifth spectrum data; determining the testing indication by performing an arbitration of the first spectrometer indication, the second spectrometer indication, the third spectrometer indication, the fourth spectrometer indication, and the fifth spectrometer indication.

In a sixth aspect, there is provided a method for permitting access to a venue for a subject, the method comprising: receiving, at a server, a testing indication from a testing device; generating, at the server, an encoded testing indication based on the testing indication; transmitting, from the server to a user device of the subject, the encoded testing indication for presentation by the subject for access to the venue.

In one or more embodiments, the generating the encoded testing indication may further comprise: encoding a time identifier and the testing indication in the encoded testing indication.

In one or more embodiments, the method may further comprise: storing, at a database, the time identifier, the testing indication, and the encoded testing indication.

In one or more embodiments, the method may further comprise: receiving, at the server from the test device, a geographic identifier of the test device; and wherein the generating the encoded testing indication may further comprise encoding the geographic identifier and the testing indication in the encoded testing indication.

In one or more embodiments, the method may further comprise: storing, at a database, the geographic identifier, the testing indication, and the encoded testing indication.

In one or more embodiments, the method may further comprise: receiving, at the server from the test device, a facial image of the subject; determining, at the server, a facial identifier based on the facial image; and wherein the generating the encoded testing indication may further comprise encoding the facial identifier and the testing indication in the encoded testing indication.

In one or more embodiments, the method may further comprise: storing, at a database, the facial identifier, the testing indication, and the encoded testing indication.

In one or more embodiments, the method may further comprise: receiving, at the server from the test device, a third-party identification number of the subject; wherein the generating the encoded testing indication further comprises encoding the third-party identification number and the testing indication in the encoded testing indication.

In one or more embodiments, the method may further comprise: storing, at a database, the third-party identification number, the testing indication, and the encoded testing indication.

In one or more embodiments, the method may further comprise: receiving, at the server, a request from the subject for a testing time slot; and transmitting, from the server to the user device, a confirmation of the testing time slot.

In one or more embodiments, the encoded testing indication may be one of the group of a barcode, a Quick Response (QR) code, and a Radio-Frequency Identifier (RFID) code.

In a seventh aspect, there is provided a system for permitting access to a venue that implements the method for permitting access to a venue of one or more embodiments.

BRIEF DESCRIPTION OF THE DRAWINGS

A preferred embodiment will now be described in detail with reference to the drawings, in which.

DESCRIPTION OF THE EXAMPLE EMBODIMENTS

Figure 1:
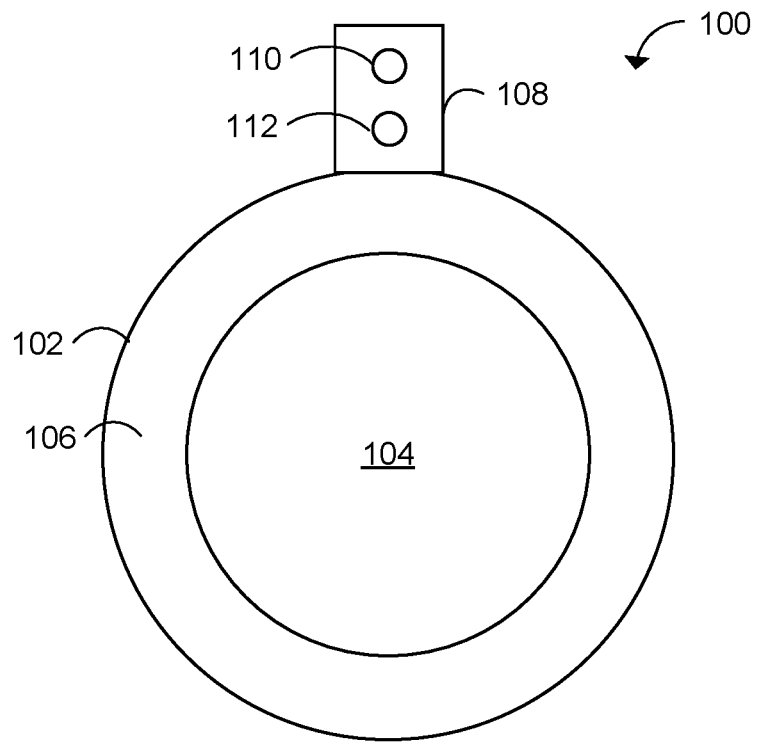
FIG. 1 is a front elevation view of a testing apparatus.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented such as hardware, software, and combinations thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmissions or downloads, magnetic and electronic storage media, digital and analog signals, and the like. The computer useable instructions may also be in various forms, including compiled and non-compiled code.

Test Apparatus

Figure 2:
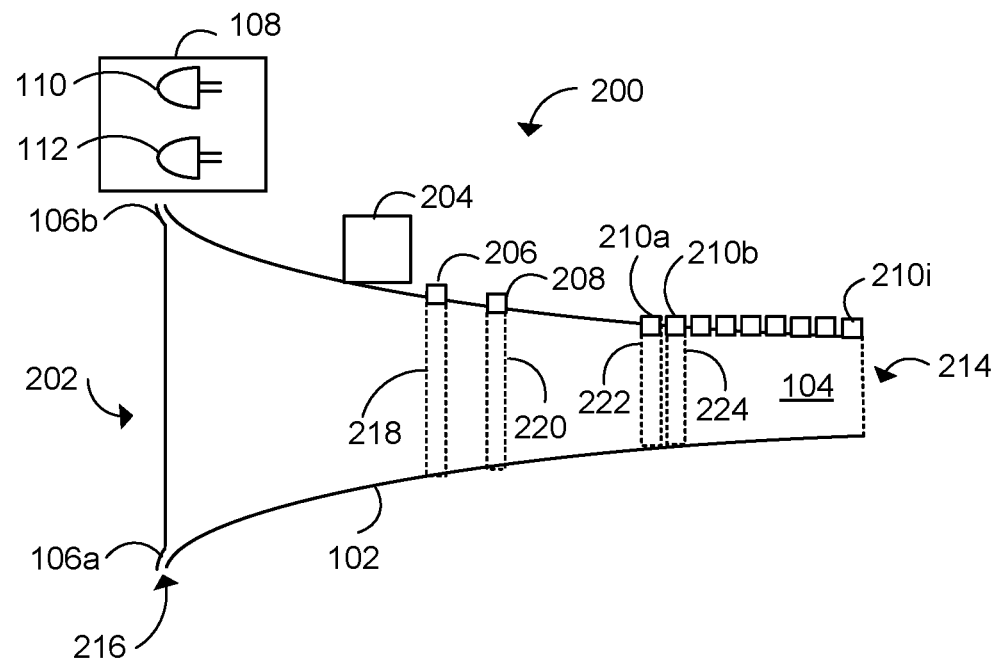
FIG. 2 is a side elevation view of the apparatus in FIG. 1.

Reference is first made to FIGS. 1-2, showing a testing apparatus 102 in accordance with a first embodiment. In the embodiment shown, the testing apparatus 102 is a non-invasive testing apparatus for a subject.

The testing apparatus has a casing 102 and a first opening 202 defining a chamber 104. The first opening 202 and the chamber 104 receive breaths from a subject positioned proximate to the first opening 202. The subject supplied breaths may be provided as normal breaths, deep breaths, coughs, sneezes, and may be provided by either the subject's mouth or nose.

The casing 102 may be generally cylindrical as shown, or may be another shape. The casing 102 may be tapered, having the first opening 202 of a larger diameter than the second opening 214.

When using the test apparatus, a subject may breathe, cough, sneeze, or otherwise provide respirations into the first opening 202 and the chamber 104. This will produce a flow in the tunnel having a particular particle size and a particular particle distribution.

Respirations including coughing may result in biological particles and/or water droplets to be communicated in the air. One or more particle detectors such as the first particle detector 206 and the second particle detector 208 may be provided in order to determine whether the number of particles provided by the subject is sufficient. Furthermore, the one or more particle detectors may determine particle size data that includes an average size of the particles/droplets expelled by the breathes (hereinafter referred to as particles). Optionally, a subject may breathe normally or may breathe more deeply, such as may be used for a breathalyzer.

There may be one or more intake members 106 proximate to the first opening 202. In one embodiment, an intake member 106 is circular, and generally formed complimentary to the casing 102. The intake member 106 may be formed to create an air flow entry port 216 between the intake member 106 and the casing 102. The air flow entry port 216 may receive air flow and form a boundary layer along the inside surface of casing 102 (see FIGS. 6-9). An advantage of the boundary layer is that the boundary layer may line the inner surface of chamber 104 and inhibit biological material being deposited thereon. A further advantage may be that the boundary layer assists in ensuring that all of the air exhaled by a subject into the testing apparatus travels through chamber 104 and does not accumulate on the inner surface of the chamber. The boundary layer may be formed, e.g., by inducing air to flow through a supplemental inlet passage extending from intake member 106 to entry port 216 due to air travelling through the chamber due to exhalation by a subject. Accordingly, the Coanada effect, a venture or an air foil shape provided at entry port 216 may be used to induce air flow in the supplemental inlet passage. Alternately, or in addition as discussed subsequently, a mechanical assist, such as a fan, may be provided.

The casing 102 may have one or more particle detector portions and one or more spectrometer portions. The particle detector portions may be, for example, transverse the chamber 104. Each of the one or more particle detector portions may have an associated particle detector. For example, the first particle detector portion 218 may have associated first particle detector 206, and the second particle detector portion 220 may have associated second particle detector 208. The spectrometer portions may also transverse the chamber 104. Each of the one or more spectrometer portions may have an associated spectrometer 210. For example, the first spectrometer portion 222 may have associated first spectrometer 210a, and second spectrometer portion 224 may have second spectrometer 210b.

The one or more particle detector portions including the first particle detector portion 218 and second particle detector portion 220 may be positioned between the first opening 202 and the one or more spectrometer portions including the first spectrometer portion 222 and the second spectrometer portion 224.

The testing apparatus 102 further has a test device 204 including a memory and a processor. The test device is in communication with the one or more spectrometers 210, the one or more particle detectors 206, 208, and the user interface 108.

The testing apparatus 102 further has an associated user interface 108. The user interface may include a red indicator 110 and a green indicator 112. The indicators may be a Light Emitting Diode (LED) or a light and/or a sound emitting member (e.g., a speaker). In one embodiment, the user interface may be a display device such as a Liquid Crystal Display (LCD), a Light Emitting Diode (LED) display or another display technology as known. The user interface 108 may be attached to the casing 102, or may be positioned nearby.

The air flow exiting the second opening 214 may be exhausted through a biological filter such as a HEPA® filter system.

The particle detector portions 218, 220 are regions of the chamber 104 through which air flows when the subject breathes. The regions comprise a volume that is monitored by a particle detector 206, 208. The particle detectors are utilized to determine if a breath or exhalation of a subject has sufficient particles for analysis by the spectrometer(s) 210. It will be appreciated that a single particle detector 218, 220 may be used. Alternately, a plurality of particle detectors 218, 220 may be used. If a plurality of particle detectors are used, then the testing apparatus may issue a signal (visual and/or auditory) if one or more of the particle detectors does not detect a sufficient number of particles and/or particles in a pre-determined size range.

The spectrometer portions 222, 224 are regions of the chamber 104 through which air flows when the subject breathes. The regions comprise a volume that is monitored by a spectrometer 210. The particle detectors are utilized to determine if a breath or exhalation of a subject has particles that conform to a pre-determined pattern indicative of the biological agent for which the subject is being tested, e.g., COVID-19. It will be appreciated that a single spectrometer 210 may be used. Alternately, a plurality of spectrometers 210 may be used. If a plurality of spectrometers 210 are used, then the testing apparatus may issue a signal (visual and/or auditory) if one or more of the spectrometers 210 detect the biological agent.

It will be appreciated that the testing apparatus may test for any biological agent other than COVID-19.

Self-Cleaning Surfaces

In one embodiment, the casing 102 and the one or more intake members 106 may be made from plastic, glass or fiberglass.

In another embodiment, the casing 102 and the one or more intake members 106 may be composed of an antiviral material such as Copper, Zinc, or Silver.

In another embodiment, the casing 102 and the one or more intake members 106 may be composed of an alloy of Copper, Zinc, and/or Silver.

In another embodiment, the casing 102 may be made from one material such as plastic, glass, or fiberglass and may have Copper, Zinc, and/or Silver or an alloy thereof deposited as a coating. The surface of the casing 102 may, for example, be coated using plasma spray or chemical vapor deposition.

Wiper

Figure 3:
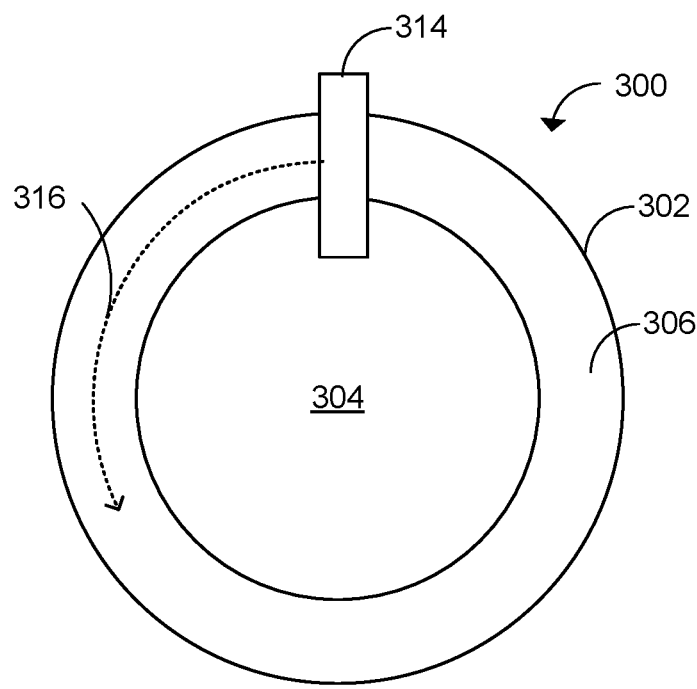
FIG. 3 is a front elevation view of an alternate apparatus of FIG. 1.
Figure 4:
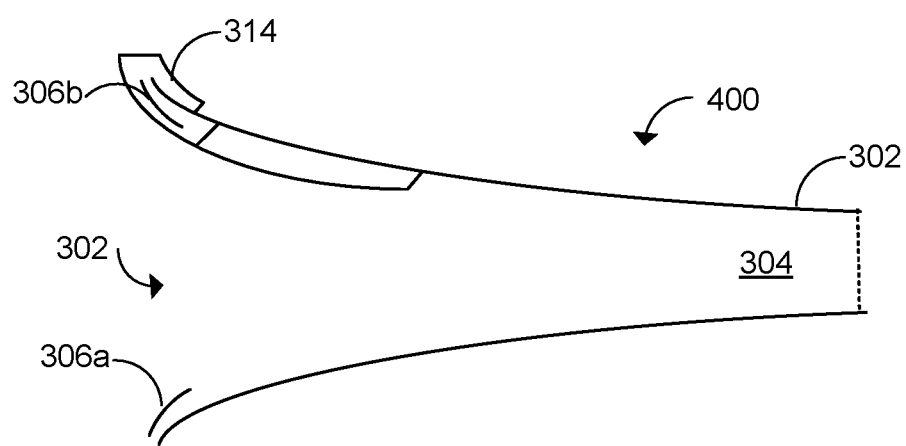
FIG. 4 is a cross-sectional view of the apparatus of FIG. 3.

Reference is next made to FIGS. 3-4, showing one embodiment of the testing apparatus 302 having a wiper 314.

The testing apparatus 302 has one or more intake members 306, and a wiper 314. The wiper 314 may be slidably attached to the casing 302, and may move circumferentially 316 relative to casing 302.

The wiper 314 may be positioned so as to clean the intake members 306 and the casing 302. The wiper 314 may extend around opening 302 from the outer surface of the casing 302, including the intake members 306, and into the chamber 304 generally along the inner surface of the casing 302.

The wiper 314 may have a cleaning surface disposed between it and the casing 302, and may clean the casing as it moves by wiping the surface of the casing. The wiper 302 may have a reservoir of liquid cleaner such as bleach or alcohol that may be dispensed onto the cleaning surface.

The wiper 314 may have a driving mechanism and may be self-driven. The driving mechanism of wiper 314 may drive one or more wheels or rollers against the casing 302 in order to move the wiper 314 around the circumference of opening 302.

The wiper 314 may perform a single rotation around the opening 302 for each sample collected by the test apparatus 302.

Similar to the casing 302 and intake members 306, the wiper may be made from or coated with an anti-viral material.

Ultraviolet Cleaning System

Referring back to FIG. 2, alternately or in addition to a wiper, the testing apparatus may have one or more ultraviolet light sources (not shown) within the chamber 104. The one or more ultraviolet light sources (not shown) may be disposed within the chamber, and positioned to provide cleaning effect on the inside surfaces of the casing 102, the intake members 106, the one or more particle detectors 206 and 208, and the one or more particle spectrometer 210.

Testing System

Figure 5:
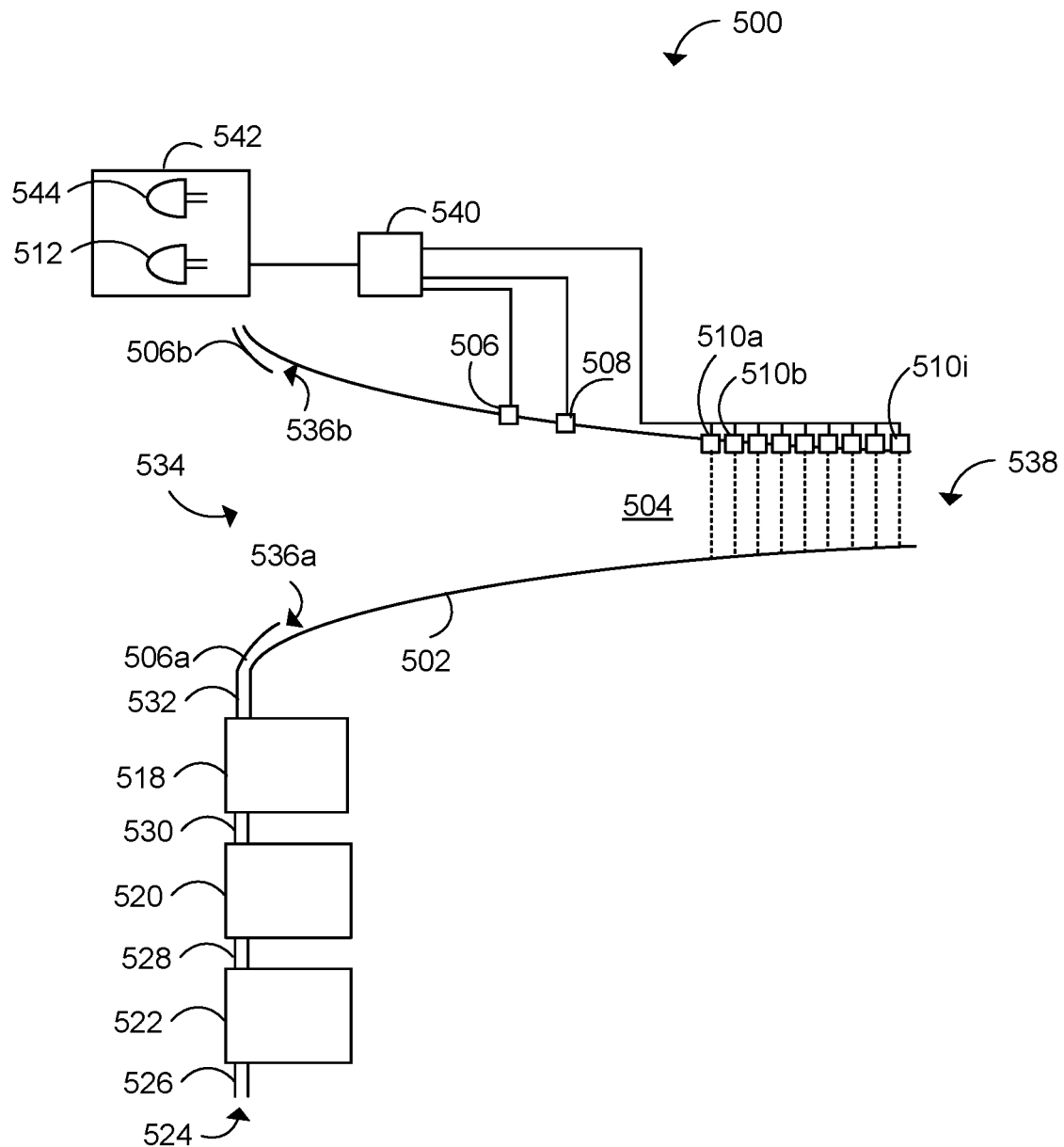
FIG. 5 is system view of the apparatus in FIG. 1.

Reference is next made to FIG. 5, there is shown a system view 500 of the test apparatus 502.

The testing system includes a testing apparatus 502 such as the one in FIGS. 1-2. The testing apparatus 502 is shown in a cross-sectional view for the sake of clarity.

The testing system may have a user interface 542, a testing device 540 having a processor and a memory, one or more particle detectors such as the first particle detector 506 and second particle detector 508, and one or more spectrometers such as first spectrometer 510a, and second spectrometer 510b.

The testing device 540 may be in communication with the user interface 542, one or more particle detectors such as first particle detector 506 and second particle detector 508, one or more spectrometers such as first spectrometer 510a and second spectrometer 510b.

A subject may submit a breath sample via the first opening 534 and into the chamber 504.

The testing apparatus 502 may have one or more intake members 506 positioned in first opening 534. The one or more intake members 506 may be positioned relative to the casing 502 to provide an air flow entry port 536 that may receive air flow from an external system.

A fan 518 may be connected to air flow entry port 536 by channel or supplemental inlet passage 532. The fan may provide air flow into the chamber 504 via air flow entry port 536.

In order to reduce or prevent contaminants entering chamber 104 via channel 532, the air entering or travelling through channel 532 may be treated to reduce the level of contaminants thereon. For example, the fan 518 may have an input from a filter system 520 via channel 530. The filter system 520 may use one or more filter media, such as HEPA® filter material. Alternately, or in addition, a cyclone 522 may be positioned in channel 532, e.g., upstream of filter system 520 such that air passes to filter system 520 from cyclone 522 via channel 528.

Optionally, a drying system (not shown) may be provided in channel 532, e.g., between the fan 518 and the air flow entry port 536 in order to reduce the humidity of the air flow into the chamber 504. The drying system (not shown) may be a refrigeration unit or a desiccant for reducing the moisture in the air drawn into the test apparatus. An advantage of using a drying system is that additional moisture (e.g., from humidity in the air) may be reduced. Additional moisture may affect the readings obtained by the spectrometer 210.

In one embodiment, the air flow exiting the air flow entry port 536 from the fan may be provided at a controlled rate.

The air flow entering the chamber via air flow entry port 536 may induce a low pressure area at first opening 534 and urge air to enter the chamber through the first opening. An advantage of this design is that the tendency for particles not entering chamber 104 during exhalation of a subject may be reduced. This urging of airflow into the chamber may urge the plurality of particles 604 in the breath sample of the subject towards the one or more particle detector portions (see FIG. 2 at 218, 220) and the one or more spectrometer portions (see e.g. FIG. 2 at 222, 224).

As shown in FIGS. 6-9, and as discussed previously, the air flow entry via air flow entry port 536 may create a boundary layer along the inner surface of casing 502. The boundary layer may also prevent particles in test samples from touching the inner surface of casing 502.

Reference is next made to FIGS. 6-9, showing a subject 602 submitting a breath sample including a plurality of particles 604 into the chamber 504. As discussed, the air flow into the chamber 504 via air flow entry port 506 creates a boundary layer of air 606 along the inner surface of chamber 504, including along the inner surface of casing 502.g.

User Interface

Figure 6:
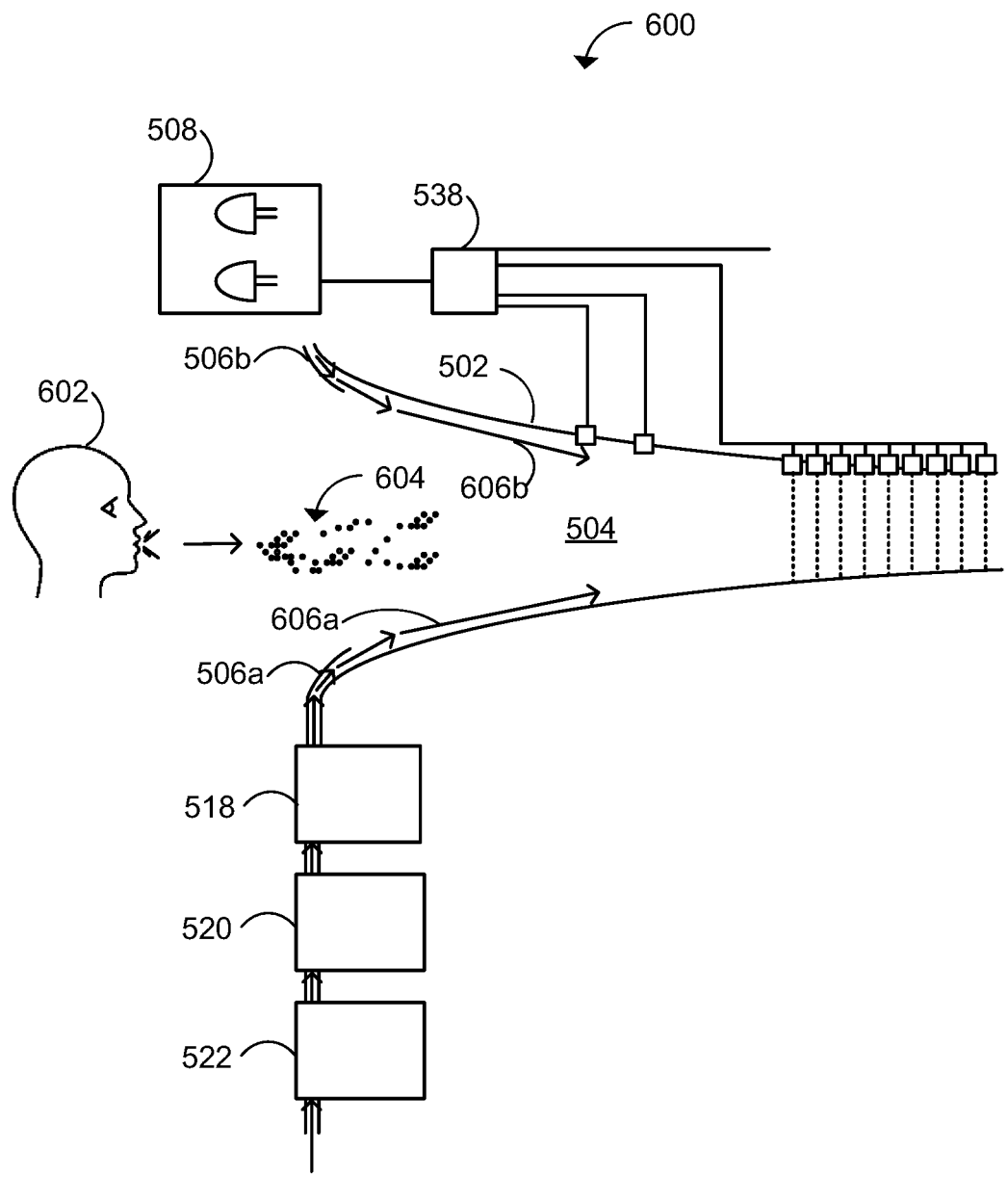
FIG. 6 is another system view of the apparatus in FIG. 1.

Referring to FIG. 6, there is shown a system view 600 of the test apparatus 502 as the subject 602 submits a breath sample into the chamber 504. The subject 602 may interact with the user interface 542, including receiving an indication of the start of the test, instructions on how to use the test apparatus, an indication of the sufficiency of their testing sample, and a test indication corresponding to the test result.

The user interface 542 may be an LCD, LED, or another display type that is in communication with the test device. In an alternate embodiment, the user interface 542 may be a pair of LEDs as shown, indicating test sufficiency with a green light illumination 544 and insufficiency with a red light illumination 512 and/or alternately a negative test result with one audio and/or visual signal such as a green light, and a positive test result with one audio and/or visual signal such as a red light.

The user interface 542 communicates to the subject 602 information and instructions about how to provide a sample (for example, how long a cough, how many coughs). The user interface 542 may be updated by the test device 540 based on particle data received from the one or more particle detectors. The particle detectors, test device 540, and user interface 542 may cooperate to ensure that the subject 602 has submitted a sufficient sample for testing.

Sample Sufficiency

Figure 7:
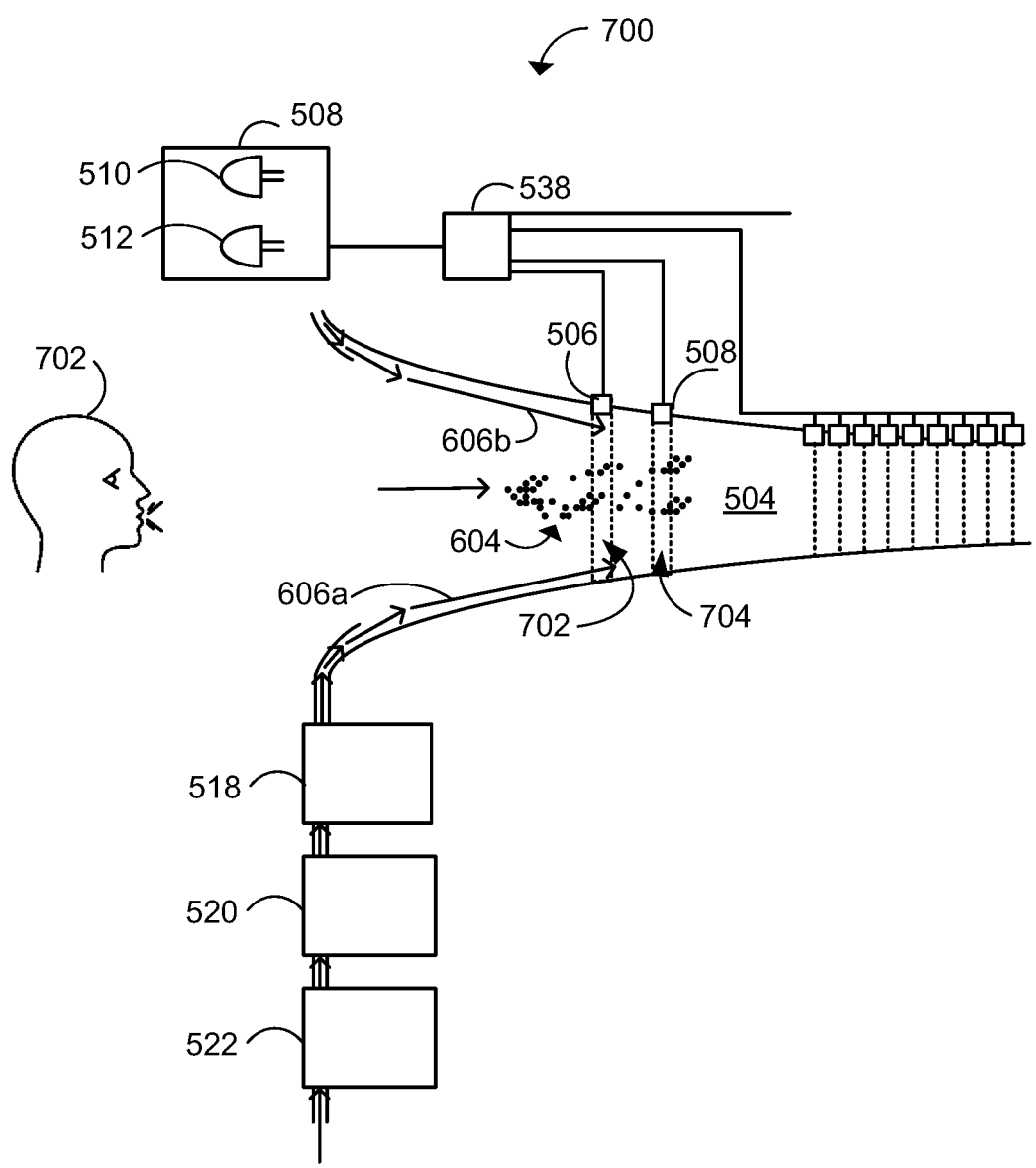
FIG. 7 is another system view of the apparatus in FIG. 1.
Figure 8:
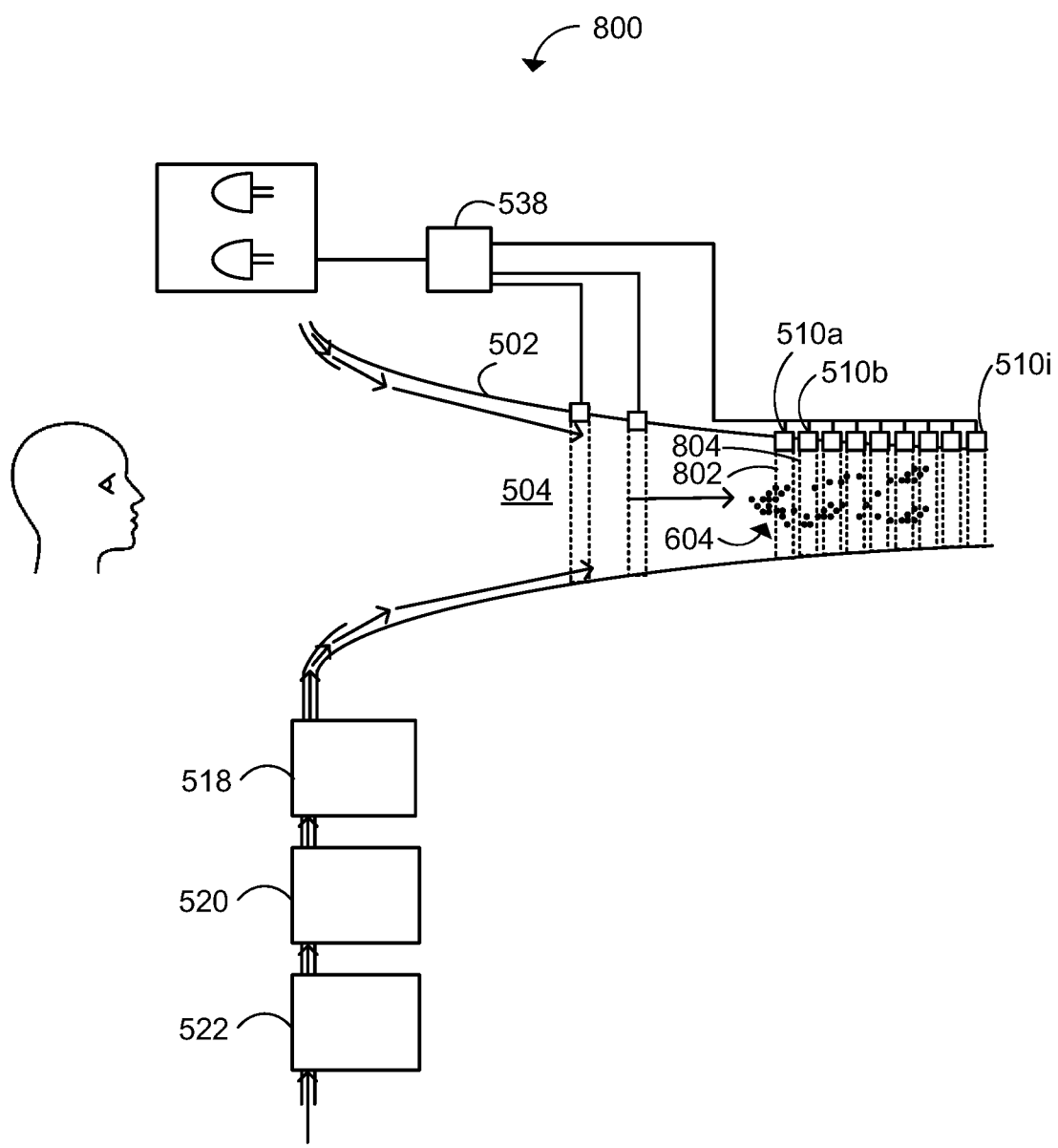
FIG. 8 is another system view of the apparatus in FIG. 1.

Referring next to FIG. 7, there is shown a system view 600 of the test apparatus 502 as the breath sample 604 from FIG. 6 travels into the chamber and enters the one or more particle detector portions.

The one or more particle detector portions, including the first particle detector portion 702 and the second particle detector portion 704 may traverse the chamber 504. As the subject's breath 604 is urged or travels through the chamber 504 and into the first particle detector portion 702, the first particle detector 506 may provide particle data (including one or more of the group of particle size information and particle count information) to the test device 504.

As the subject's breath 604 further passes into the second particle detector portion 704, the second particle detector 508 may also provide particle data to the test device 504.

The particle detectors 506 and 508 may sense at least one of the group of particle size and particle count. The particle detectors may provide ensemble measurements or single particle measurements. The ensemble measurements may include information about the entire breath particle dispersion. The ensemble measurements may be provided as a sum value, or an average value. The single particle measurements may give the measurements of individual particles, and where used the particle detector may provide a plurality of individual particle measurements.

The particle detectors may be laser diffraction detectors. The particle detectors may provide readings of the particles in the breath sample. The detectors may be detectors that are suitable for detecting standard size particles in air exhaled by a person. Accordingly, the detectors may be detectors that can detect particles that are in a particular particle size range, e.g., from between 0.1 to 2000 µm, 0.5 to 1000 µm or the like. The particle data may be sent to the test device 540 in real-time as the breath passes through the particle detector portion 702. The particle data may be sent to the test device 540 at a very high frequency, for example, 10,000 measurements per second.

Optionally, the first particle detector and the second particle counter may be of different designs, for example first particle detector may be a a detector for detecting particles that are in a lower part of the particle size range and the second particle detector may be a detector for detecting particles that are in an upper part of the particle size range.

Figure 10:
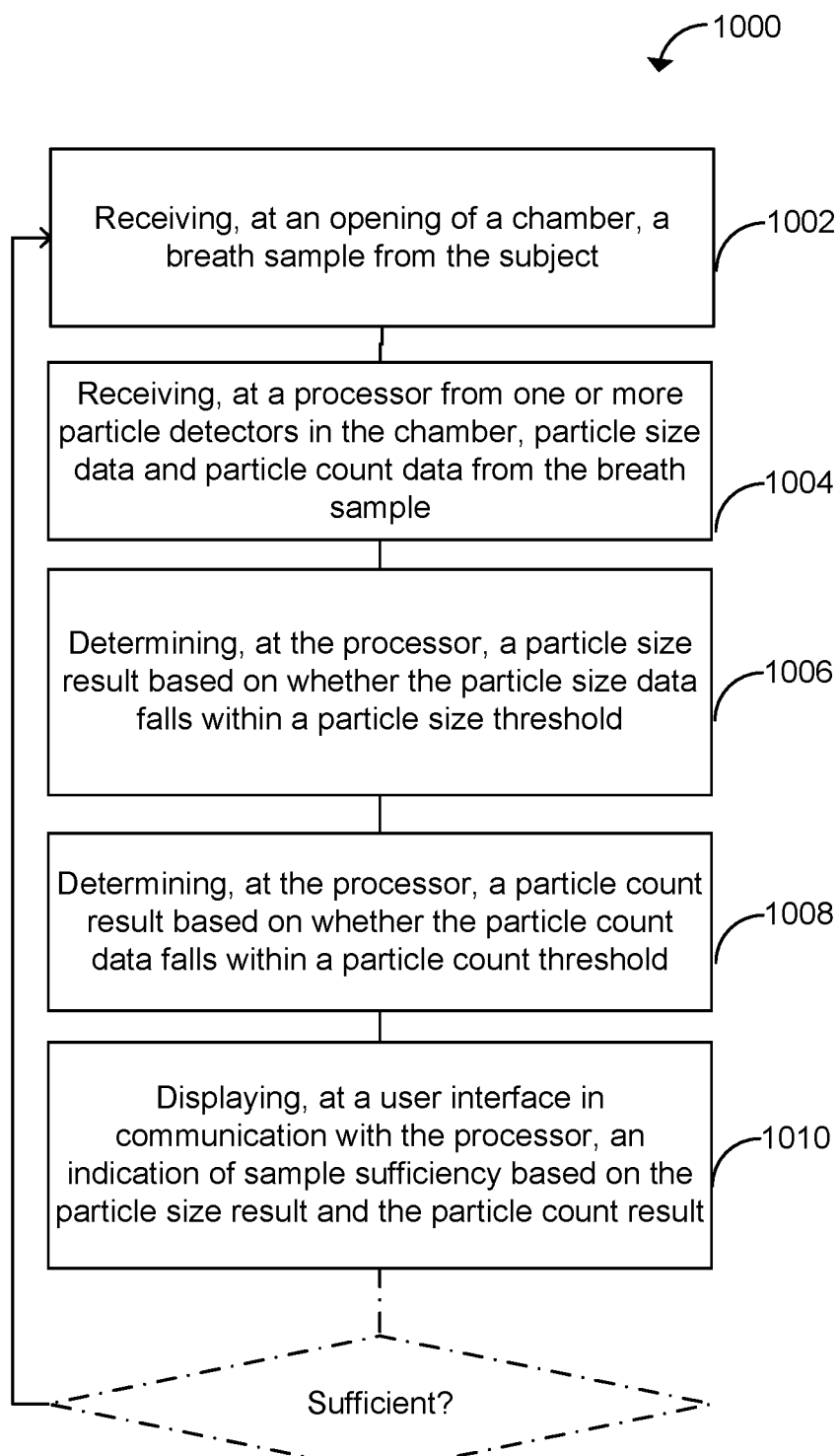
FIG. 10 is a process flow for testing a subject.

The test device 504 may have a processor for executing a method of determining sample sufficiency, such as the one in FIG. 10.

Referring next to FIG. 10, there is shown a process flow 1000 for determining sample sufficiency.

An insufficient sample may mean that there have been test collection issues with the subject. This may be because the subject has not coughed or breathed heavily enough and thus not provided a sufficient number of particles to analyze. A particle count threshold may be determined in order to set an operating window for the testing apparatus. The particle count threshold may include a lower bound and an upper bound, and breath samples outside of either condition may mean the subject has to provide a new breath sample or additional breaths to the current sample.

Another sample may be insufficient if the particle size is too large or too small. This may be because the subject has a disease causing larger particles to be expelled from the subject when they breathe or cough. A particle size threshold may be determined in order to set an operating window for the testing apparatus. The particle size threshold may include a lower bound and an upper bound, and breath samples outside of either condition may mean the subject has to provide a new breath sample or additional breaths to the current sample. The particle size threshold may have a lower bound of 100 nm and an upper bound of 150 nm.

In one embodiment, the particle size information is checked against its threshold conjunctively when the particle count information is checked against its threshold in order to determine the sufficiency of a sample.

In another embodiment, the particle size information is considered first against its threshold, and then once it is determined the particle size is sufficient, the particle count information is considered against the particle count threshold.

In one embodiment, the particle size information from the one or more particle detectors may be used in order to determine a testing indication for the subject.

If a sample is determined to be insufficient by the test device 540, an indication of the insufficient sample may be output to user interface 542.

In one embodiment, the particle data from all of the one or more particle detectors is considered together using an arbitration or an election between the collected data.

In another embodiment, the particle count data is summed for each particle detector in the one or more particle detectors and the particle size data is averaged across all of the detectors in the one or more particle detectors.

In one embodiment, there is a method provided for determining a sample sufficiency for non-invasive respiratory testing of a subject.

At 1002, receiving, at an opening of a chamber, a breath sample from the subject.

At 1004, receiving, at a processor from one or more particle detectors in the chamber, particle size data and particle count data from the breath sample.

At 1006, determining, at the processor, a particle size result based on whether the particle size data falls within a particle size threshold.

At 1008, determining, at the processor, a particle count result based on whether the particle count data falls within a particle count threshold.

At 1010, displaying, at a user interface in communication with the processor, an indication of sample sufficiency based on the particle size result and the particle count result.

Optionally, if the indication of sample sufficiency indicates an insufficient sample state, displaying, at the user interface, an indication for the user to contribute an additional sample.

Optionally, the particle size data and particle count data are received from two or more particle detectors in the chamber.

Optionally, the method may further include: receiving, at the processor from a proximity detector, subject distance data; determining, at the processor, a subject distance result based on whether the subject distance falls within a subject distance threshold; and wherein the indication of sample sufficiency further comprises an indication for the user to move closer and contribute an additional sample.

Figure 12:
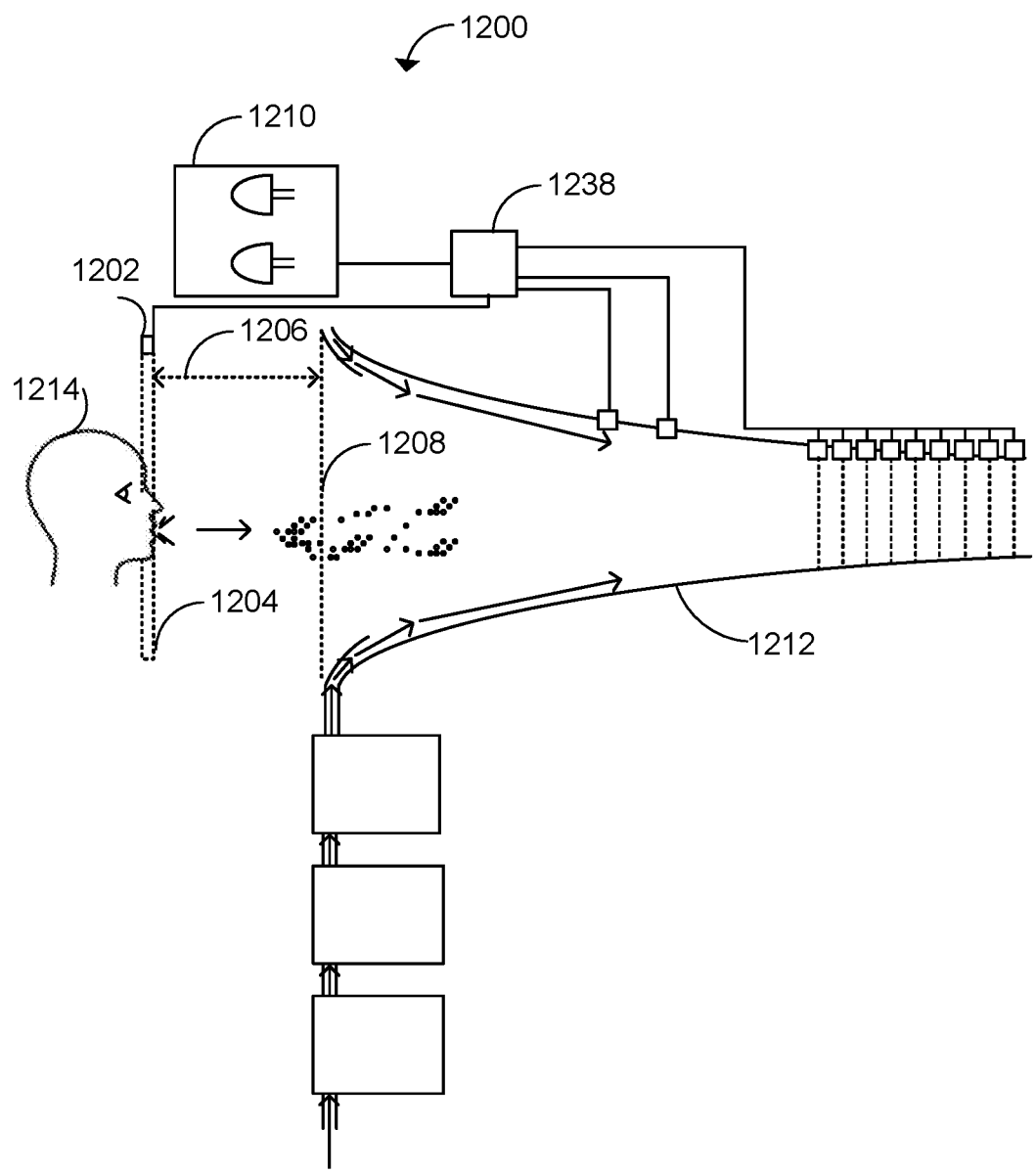
FIG. 12 is a system view of an alternate apparatus.

Optionally, the proximity detector is a light curtain as described with respect to the embodiment of FIG. 12.

Proximity Detector

Reference is next made to FIG. 12, there is shown a system view 1200 of an alternate embodiment of the apparatus in FIGS. 1-2.

Optionally, in any embodiment herein, a proximity detector 1202 may be provided in order to notify the subject if they are too far away from the test apparatus 1212. In one embodiment, the proximity detector 1202 may be a video camera. In another embodiment, the proximity detector may be an LED light curtain.

The proximity detector 1202 may determine if the subject 1214 has positioned their head within the plane 1204, and therefore satisfying the maximum distance requirement 1206. The maximum distance requirement 1206 may be measured from the proximity detector plane 1204 and a first opening plane 1208 of the test apparatus.

In the case where a subject 1214 does not meet the maximum distance requirement 1206, the test device 1238 may display an indication accordingly on the user interface 1210.

Spectrometer & Spectrometer Arbitration

Referring back to FIG. 8, there is shown another system view 800 of the test apparatus 502 as the breath sample 604 from FIG. 6 travels into the chamber and enters the one or more spectrometer portions.

The spectrometers 510 may provide an absorption spectrum of particles, including an absorption profile over a plurality of wavelengths.

The one or more spectrometer portions, including the first spectrometer portion 802 and the second spectrometer portion 804 may traverse the chamber 504. As the subject's breath 604 travels through the chamber 504 and into the first spectrometer portion 802, the first spectrometer 510a may provide spectrum data (including an absorption curve) to the test device 504.

As the subject's breath 604 further passes into the second spectrometer portion 804, the second spectrometer 510b may also provide spectrum data to the test device 504.

In one embodiment, each spectrometer in the one or more spectrometers may take multiple spectrum measurements, and the spectrum data may be provided to the test device 540 including a time reference of collection. The measurement by the one or more spectrometers may be continuous during the testing window for the subject.

While 9 spectrometers 510 are shown in FIGS. 2, 5, 6, 7, 8, 9, and 12, there may be more or less provided that, optionally, the number of spectrometers remains odd. The number of spectrometers may be configurable by an end user of the test apparatus. For example, for an extremely high assurance venue like a Neonatal Intensive Care Unit (NICU), a test apparatus with 11 or 13 spectrometers might be used in the test apparatus. For example, for a low to medium assurance venue like a shopping mall or a national park, 1 or 3 spectrometers might be used in the test apparatus.

Optionally, the one or more spectrometers may be a plurality of different spectrometer types, including different laser types and different designs.

In one embodiment, the test device 540 may determine a test indication for the subject based upon the spectrum data (including a plurality of time based results) from the one or more spectrometers. The test indication may be determined by the test device 540 based on an election of individual spectrometer indications determined from each spectrometer. For example, if there are 3 spectrometers, and an individual spectrometer indication is determined based on the spectrum data of each spectrometer, and 2 of the 3 spectrometers identify a positive test result, the resulting elected indication may also be positive. On the contrary, if only 1 of the 3 spectrometers identifies a positive test result, the resulting elected indication may be negative. The election threshold for such determinations may be configurable by a user. The election threshold for such determinations may be configurable.

In another embodiment, sensor fusion of the spectrum data from the multiple different spectrometers may be used in order to combine the data and determine a test indication based on the combined measurements of the one or more spectrometers. Sensor fusion may also be used across the series of spectrum data in a time interval in order to determine a test indication.

Figure 11:
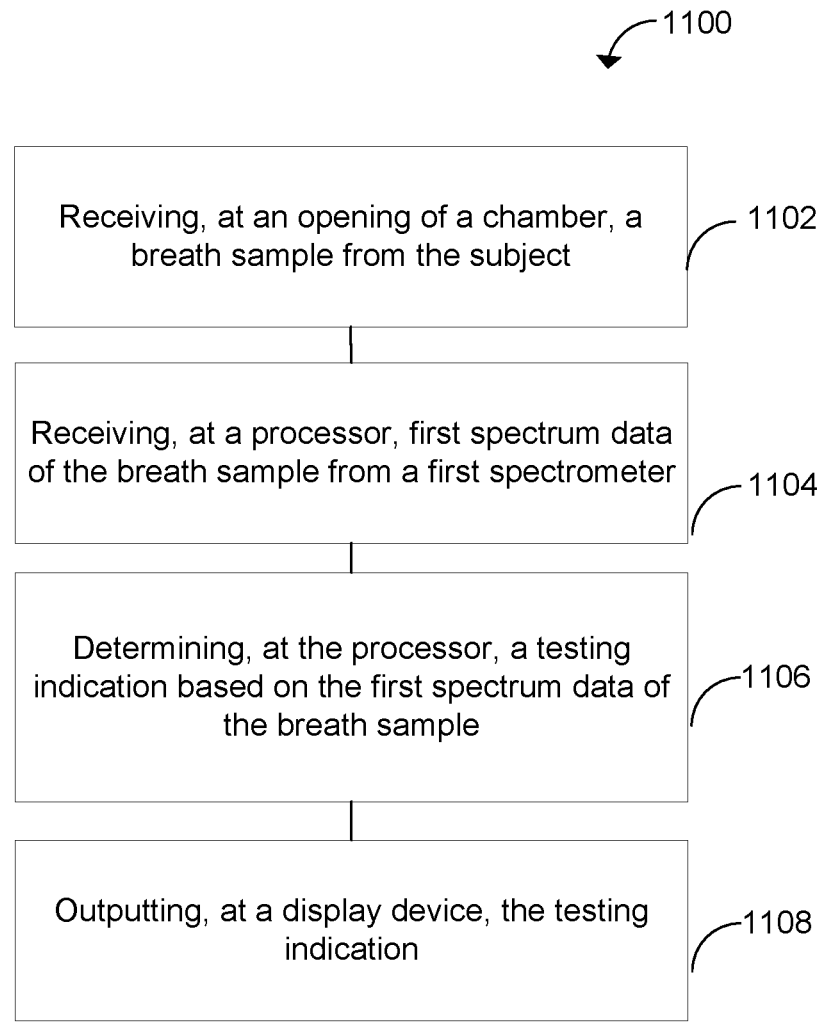
FIG. 11 is another process flow for testing a subject.

Reference is next made to FIG. 11, which shows a process flow 1100 for determining a test indication for a subject.

In order to make a test indication for a subject, spectrum data from multiple spectrometers may be used. This may result in situations where the spectrum data, when taken individually at each spectrometer, may be in disagreement.

In order to provide a test indication for the user, an election may be used of the individual test indications of each spectrometer.

Furthermore, sensor fusion may be used in order to combine the spectrum data from each of the one or more spectrometers into a signal set of spectrum data in order to make a test indication for a subject.

In an embodiment, a method is provided for providing a test indication for a subject.

At 1102, receiving, at an opening of a chamber, a breath sample from the subject.

At 1104, receiving, at a processor, first spectrum data of the breath sample from a first spectrometer.

At 1106, determining, at the processor, a testing indication based on the first spectrum data of the breath sample.

At 1108, outputting, at a display device, the testing indication.

Optionally, the method may further comprise: receiving, at the processor, second spectrum data from a second spectrometer; receiving, at the processor, third spectrum data from a third spectrometer; wherein the testing indication is determined based on the first spectrum data, the second spectrum data, and the third spectrum data.

Optionally, the determining, at the processor, a testing indication further comprises performing sensor fusion on the first spectrum data, the second spectrum data, and the third spectrum data.

Optionally, the determining, at the processor, a testing indication further comprises: determining a first spectrometer indication based on the first spectrum data; determining a second spectrometer indication based on the second spectrum data; determining a third spectrometer indication based on the third spectrum data; determining the testing indication by performing an arbitration of the first spectrometer indication, the second spectrometer indication, and the third spectrometer indication.

Optionally, the determining, at the processor, a testing indication further comprises: receiving, at the processor, fourth spectrum data from a fourth spectrometer; receiving, at the processor, fifth spectrum data from a fifth spectrometer; determining a fourth spectrometer indication based on the fourth spectrum data; determining a fifth spectrometer indication based on the fifth spectrum data; determining the testing indication by performing an arbitration of the first spectrometer indication, the second spectrometer indication, the third spectrometer indication, the fourth spectrometer indication, and the fifth spectrometer indication.

Optionally, the determining, at the processor, a testing indication further comprises: receiving, at the processor, sixth spectrum data from a sixth spectrometer; receiving, at the processor, seventh spectrum data from a seventh spectrometer; determining a sixth spectrometer indication based on the sixth spectrum data; determining a seventh spectrometer indication based on the seventh spectrum data; determining the testing indication by performing an arbitration of the first spectrometer indication, the second spectrometer indication, the third spectrometer indication, the fourth spectrometer indication, the fifth spectrometer indication, the sixth spectrometer indication, and the seventh spectrometer indication.

Optionally, the determining, at the processor, a testing indication further comprises: receiving, at the processor, eighth spectrum data from an eighth spectrometer; receiving, at the processor, ninth spectrum data from a ninth spectrometer; determining an eighth spectrometer indication based on the eighth spectrum data; determining a ninth spectrometer indication based on the ninth spectrum data; determining the testing indication by performing an arbitration of the first spectrometer indication, the second spectrometer indication, the third spectrometer indication, the fourth spectrometer indication, the fifth spectrometer indication, the sixth spectrometer indication, the seventh spectrometer indication, the eighth spectrometer indication, and the ninth spectrometer indication.

Optionally, the determining, at the processor, a testing indication further comprises: receiving, at the processor, sixth spectrum data from a sixth spectrometer; receiving, at the processor, seventh spectrum data from a seventh spectrometer; determining a sixth spectrometer indication based on the sixth spectrum data; determining a seventh spectrometer indication based on the seventh spectrum data; determining the testing indication by performing an arbitration of the first spectrometer indication, the second spectrometer indication, the third spectrometer indication, the fourth spectrometer indication, the fifth spectrometer indication, the sixth spectrometer indication, and the seventh spectrometer indication.

Optionally, the determining, at the processor, a testing indication further comprises: receiving, at the processor, eighth spectrum data from an eighth spectrometer; receiving, at the processor, ninth spectrum data from a ninth spectrometer; determining an eighth spectrometer indication based on the eighth spectrum data; determining a ninth spectrometer indication based on the ninth spectrum data; determining the testing indication by performing an arbitration of the first spectrometer indication, the second spectrometer indication, the third spectrometer indication, the fourth spectrometer indication, the fifth spectrometer indication, the sixth spectrometer indication, the seventh spectrometer indication, the eighth spectrometer indication, and the ninth spectrometer indication.

Figure 9:
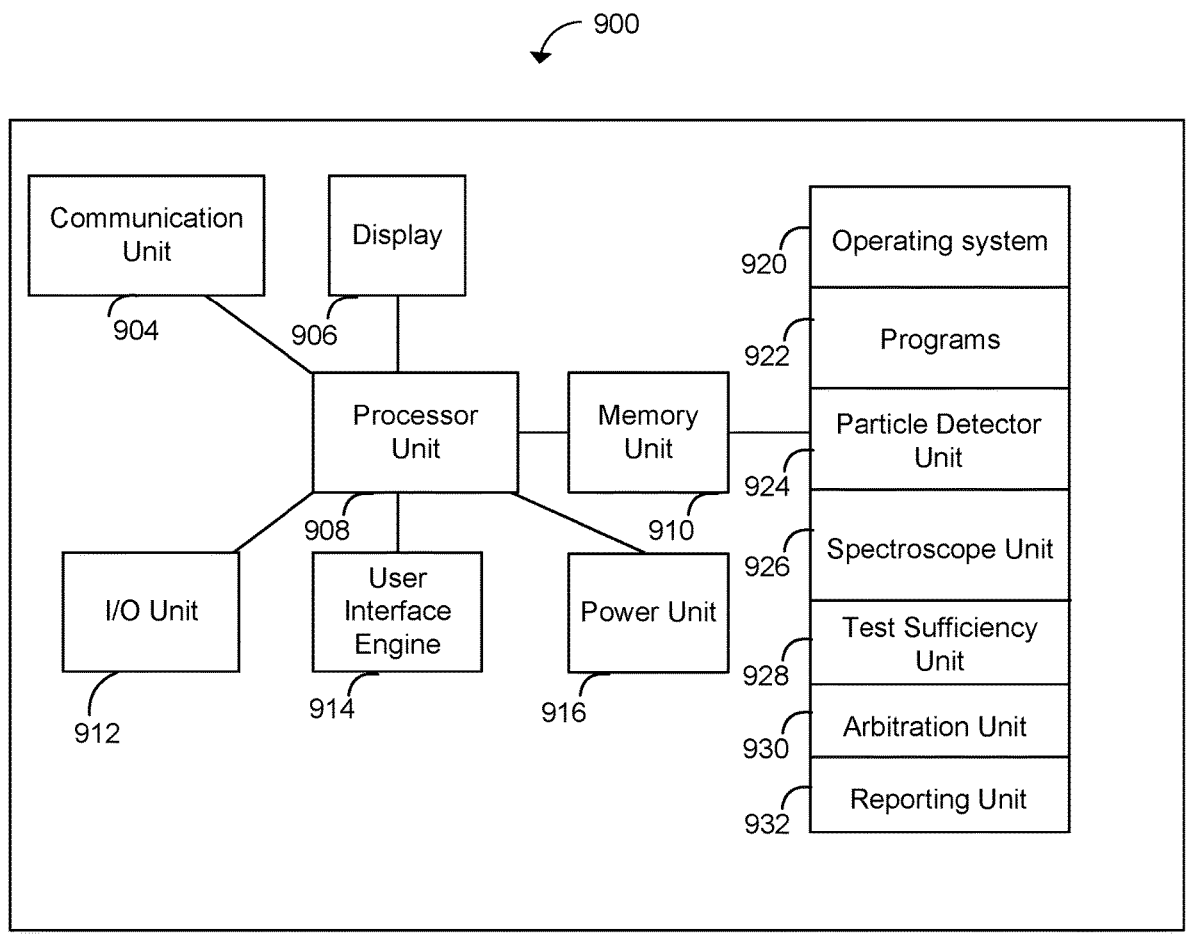
FIG. 9 is a test device of a testing apparatus.

Reference is next made to FIG. 9, showing a test device 900 such as the test devices in FIGS. 2, 5, 6, 7, and 8.

The test device 900 includes a communication unit 904, a processor unit 908, a memory unit 910, I/O unit 912, a user interface engine 914, and a power unit 916.

The processor unit 908 controls the operation of the test device 900. The processor unit 908 can be any suitable processor, controller or digital signal processor that can provide sufficient processing power depending on the configuration, purposes and requirements of the test device 900 as is known by those skilled in the art. For example, the processor unit 908 may be a high performance general processor. In alternative embodiments, the processor unit 908 can include more than one processor with each processor being configured to perform different dedicated tasks. In alternative embodiments, it may be possible to use specialized hardware to provide some of the functions provided by the processor unit 908. For example, the processor unit 908 may include a standard processor, such as an Intel® processor, an ARM® processor or a microcontroller.

The communication unit 904 can include wired or wireless connection capabilities. The communication unit 904 can include a radio that communicates utilizing 4G, LTE, 5G, CDMA, GSM, GPRS or Bluetooth protocol according to standards such as IEEE 802.11a, 802.11b, 802.11g, or 802.11n, etc. The communication unit 904 can be used by the test device 900 to communicate with other devices or computers.

The processor unit 908 can also execute a graphical user interface (GUI) engine 914 that is used to generate various user interfaces.

The user interface engine 914 is configured to generate interfaces for subjects to receive test indications, sufficiency indications, and to provide information and instructions to a subject, etc. The various interfaces generated by the user interface engine 914 are displayed to the subject on display 108 (see FIG. 1-2).

The display 906 may be the user interface 108 (see FIGS. 1-2) and may include a red indicator 110 and a green indicator 112. The indicators may be a Light Emitting Diode (LED) or a light. In one embodiment, the user interface may be a display device such as a Liquid Crystal Display (LCD), a Light Emitting Diode (LED) display or another display technology as known.

The I/O unit 912 can include at least one of a mouse, a keyboard, a touch screen, a thumbwheel, a track-pad, a track-ball, a card-reader, voice recognition software and the like again depending on the particular implementation of the test device 900. In some cases, some of these components can be integrated with one another.

The power unit 916 can be any suitable power source that provides power to the test device 900 such as a power adaptor or a rechargeable battery pack depending on the implementation of the test device 900 as is known by those skilled in the art.

The memory unit 910 comprises software code for implementing an operating system 920, programs 922, particle detector unit 924, spectroscope unit 926, test sufficiency unit 928, arbitration unit 930, and reporting unit 932.

The memory unit 910 can include RAM, ROM, one or more hard drives, one or more flash drives or some other suitable data storage elements such as disk drives, etc. The memory unit 910 is used to store an operating system 920 and programs 922 as is commonly known by those skilled in the art. For instance, the operating system 920 provides various basic operational processes for the test device 900. For example, the operating system 920 may be a mobile operating system such as Google Android operating system, or Apple iOS operating system, Raspberry Pi, or another operating system.

The programs 922 include various user programs so that a user can interact with the test device 900 to perform various functions such as, but not limited to, receiving, transforming, outputting, decoding, and encoding various data for the test device.

The memory unit 910 may further comprise a database (not shown) for storing the particle detector data from the one or more particle detectors, and the spectrum data from the one or more spectrometers.

The particle detector unit 924 receives particle detector data from the one or more particle detectors via I/O Unit 912. The received particle detector data may be high frequency data, and may be in a variety of different formats. The particle detector data may be transmitted and received using an i2c bus, CANBUS, serial connection, parallel connection, or any other data connection as known. The particle detector unit 924 may prepare the received particle detector data by averaging the signal, reducing noise, or other pre-processing tasks. The particle detector unit 924 may store the particle detector data in the database (not shown) in memory unit 910.

The spectroscope unit 926 receives spectrum data from the one or more spectroscopes via I/O Unit 912. The received spectrum data may be high-frequency data and may be in a variety of formats. Generally, the spectrum data may be an absorption spectrum received from the spectroscope. The spectrum data may be transmitted and received using an i2c bus, CANBUS, serial connection, parallel connection, or any other data connection as known. The spectroscope unit 924 may prepare the received spectrum data by averaging the signal, reducing noise, or other pre-processing tasks. The spectroscope unit 926 may store the spectrum data in the database (not shown) in memory unit 910.

The test sufficiency unit 928 may use the particle detector data stored in the database (not shown) in memory unit 910 and apply the method described in FIG. 10 in order to determine a test sufficiency indication.

The arbitration unit 930 may use the spectrum data stored in the database (not shown) in memory unit 910 and apply the method described in FIG. 11 in order to determine a test indication.

Optionally, the arbitration unit 930 may also use the particle detector data in order to determine a test indication.

The reporting unit 932 may determine a test report based on particle detector data, spectrum data, the test indication, and any subject information submitted to the test device in order to identify the subject (for example, a facial image, a third-party identification number such as a driver's license number, etc.).

The reporting unit 934 may transmit the test indication along with the particle detector data, spectrum data, and any subject information submitted to the test device in order to identify the subject to a server using communication unit 904.

Figure 13:
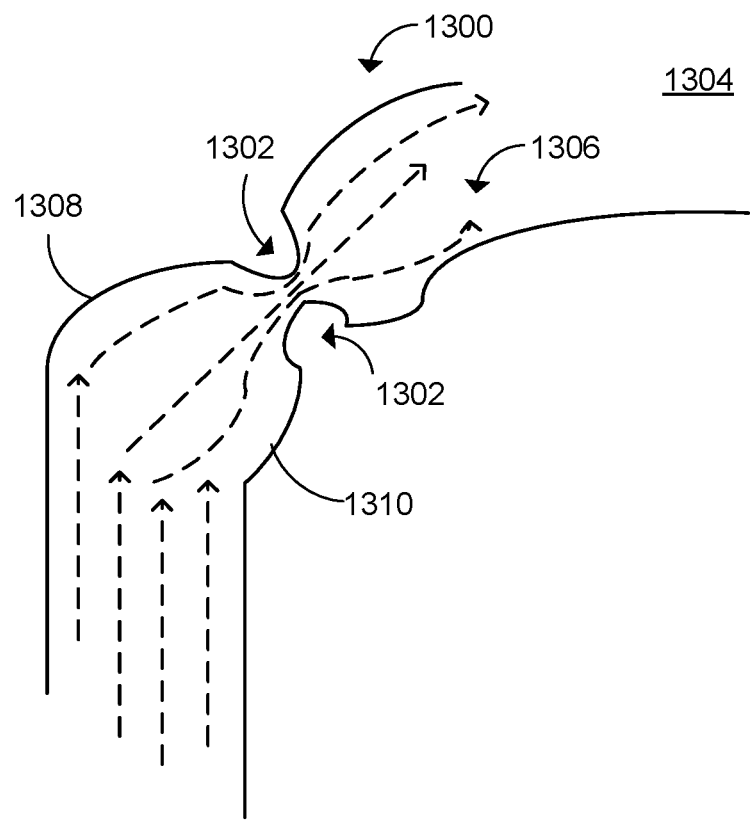
FIG. 13 is a partial cross-sectional view of an alternate apparatus.

Reference is next made to FIG. 13, which shows a partial cross-sectional view 1300 of an alternate apparatus.

In an alternate embodiment, the air flow is received at air flow entry port 1306 into the chamber 1304 via a constricted section 1302. The constricted section 1302 may be formed between the intake member 1308 and the casing 1310.

Test Tracking and Mobile Passes

Figure 14:
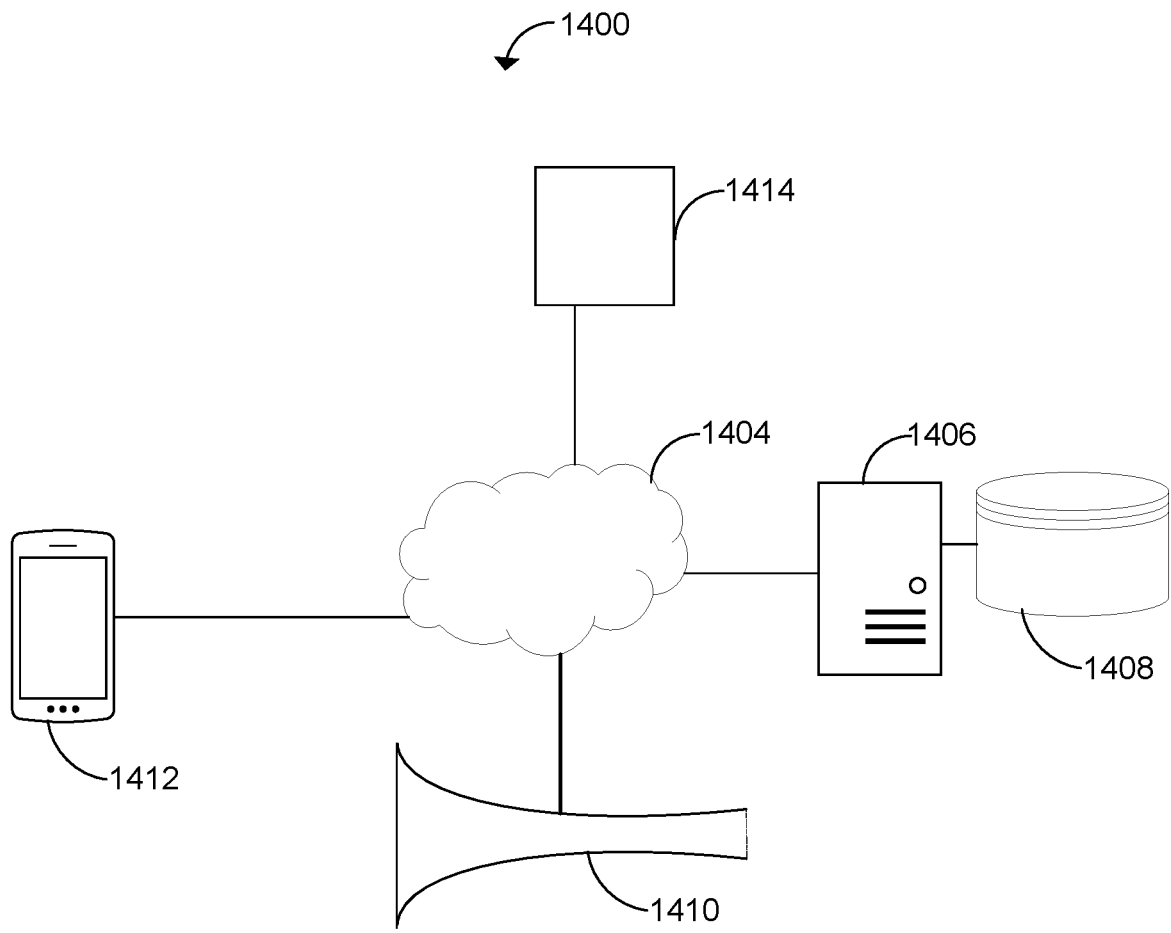
FIG. 14 is a system view for allowing access to a venue.

Referring next to FIG. 14, there is shown a system view 1400 for generating test passes for access to venues. As exemplified, the system 1400 may have a network 1404, a server 1406, a database 1408, a test device 1410, a mobile device 1412, and a venue 1414.

The network 1404 may be any network or network components capable of carrying data including the Internet, Ethernet, fiber optics, satellite, mobile, wireless (e.g. Wi-Fi, WiMAX), SS7 signaling network, fixed line, local area network (LAN), wide area network (WAN), a direct point-to-point connection, mobile data networks (e.g., Universal Mobile Telecommunications System (UMTS), 3GPP Long-Term Evolution Advanced (LTE Advanced), Worldwide Interoperability for Microwave Access (WiMAX), etc.) and others, including any combination of these.

A user device 1412 may be any two-way communication device with capabilities to communicate with other devices. A user device 1412 may be mobile devices such as mobile devices running the Google® Android® operating system or Apple® iOS® operating system.

Each user device 1412 includes and executes a client application, such as a digital pass application, to receive, store, and present test indications in the form of test passes. The client application may be a web application provided by server 1406 of test pass system 1400, or it may be an application installed on the user device 1412, for example, via an app store such as Google® Play® or the Apple® App Store®

As shown, the user devices 1412 are configured to communicate with server 1406 using network 1404. For example, server 1406 may provide a web application or Application Programming Interface (API) endpoint for an application running on user device 1412.

The server 1406 is any networked computing device or system, including a processor and memory, and is capable of communicating with a network, such as network 1404. The server 1406 may include one or more systems or devices that are communicably coupled to each other. The computing device may be a personal computer, a workstation, a server, a portable server, or a combination of these.

The server 1406 manages the test passes generated by test device 1410 and facilitates the generation, storage, and presentation of the passes. For example, the server 1406 may allow a subject to create accounts, add test indications including encoded test indications associated with a subject account, and present a test pass including a test indication or an encoded test indication at a venue, etc. The plurality of subject accounts, the test passes, test indications (including encoded test indications), and other subject information, may be stored in a database 1408.

The database 1408 may be a Structured Query Language (SQL) such as PostgreSQL or MySQL or a not only SQL (NoSQL) database such as MongoDB, or Graph Databases etc.

The testing device 1410 may be a testing device according to the present embodiments, or may be another testing device as known.

A test pass may be generated by the test device 1410 and/or the server 1406. It will be appreciated that the test pass may be generated by any part of the system based on the results of a test conducted using a test device. A test pass may be a human readable or machine readable document and may include the subject's test indication, encoded information, or other information about the subject. This test pass may be verified by a venue reading the test pass by sending a verification request the server 1406. This may include a time the test was recorded, a geographic indication of where the test was performed, a facial image for facial recognition of the subject (or a facial identifier determined from the facial image), and a third-party identification number. In an alternate embodiment, it will be appreciated that the test pass may be generated at the venue. For example, the test pass may be stored in a database at the venue and accessible by, e.g., an attendant who monitors an entrance to the venue and/or an automated entrance, such are in use in immigration lounges in airports. In such a case a subject may identify themselves at the venue and be admitted based on a test pass that is available at the venue. In such a case, a the system need not include an end user device 1412.

The test pass, including the encoded testing indication may be stored in a database 1408 in communication with server 1406.

A subject attends to a test device 1410 in order to get a test indication. The subject may receive a test pass including a test indication (including an encoded test indication) at the mobile device 1412. Subjects who receive a test indication may present it at a venue in order to access the venue. For example, a subject may receive an encoded test indication at mobile device 1412 and may display it at the venue for admission, such as to an attendant who monitors an entrance to the venue and/or it may be used at an automated entrance, such are in use in immigration lounges in airports.

Large venues where individuals may be in close proximity include theatres, shopping malls, museums, zoos, cruise ships, offices, airplanes, hospitals, buses, and the like.

In one embodiment, a system and method is provided for generating test passes for subjects such that they may be permitted access while mitigating the risk to others in the case of a communicable disease. Optionally, the test pass may be obtained by a subject being tested at one location (e.g., a kiosk that is distal to the venue) and then, at a later time, seeking admission at a second location based on the test pass. An advantage of this embodiment is that people seeking admission to an venue need not be tested at the venue but may be permitted admission based on a test conducted, e.g., earlier in a day or a day or two earlier at a separate location from the venue.

Figure 15:
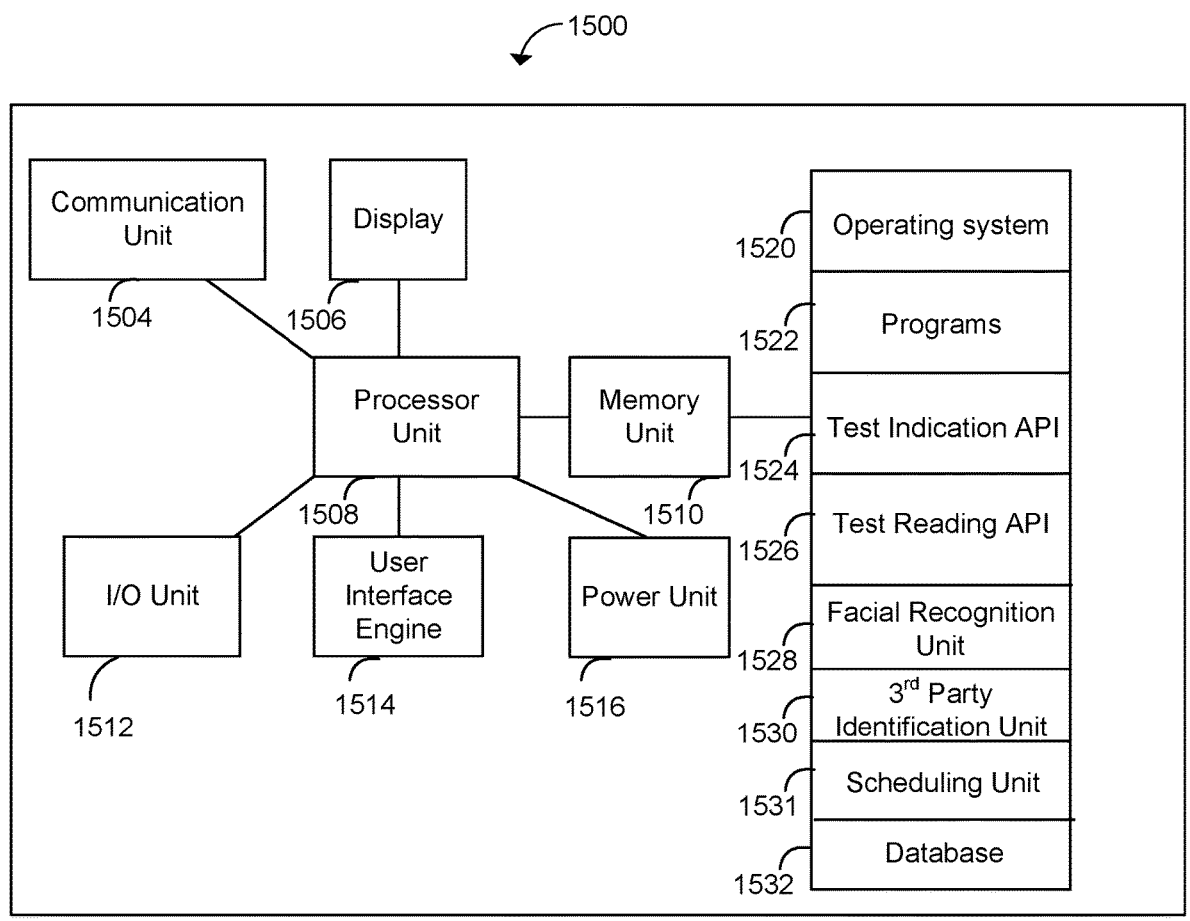
FIG. 15 is a server of the system for allowing access to a venue.

Reference is next made to FIG. 15, which shows a server 1500 of the system of FIG. 14.

The server 1500 includes a communication unit 1504, a processor unit 1508, a memory unit 1510, I/O unit 1512, a user interface engine 1514, and a power unit 1516.

The processor unit 1508 controls the operation of the server 1500. The processor unit 1508 can be any suitable processor, controller or digital signal processor that can provide sufficient processing power depending on the configuration, purposes and requirements of the server 1500 as is known by those skilled in the art. For example, the processor unit 1508 may be a high performance general processor. In alternative embodiments, the processor unit 1508 can include more than one processor with each processor being configured to perform different dedicated tasks. In alternative embodiments, it may be possible to use specialized hardware to provide some of the functions provided by the processor unit 1508. For example, the processor unit 1508 may include a standard processor, such as an Intel® processor, or an AMD® processor.

The communication unit 1504 can include wired or wireless connection capabilities. The communication unit 1504 can include support for wired (for instance Ethernet) and wireless communication (for instance IEEE 802.11a, 802.11b, 802.11g, or 802.11n, etc). The communication unit 1504 can be used by the server 1500 to communicate with other devices or computers.

The processor unit 1508 can also execute a graphical user interface (GUI) engine 1514 that is used to generate various user interfaces.

The display 1506 may provide for administration of the server 1500. In one embodiment, the display device may be a Liquid Crystal Display (LCD), a Light Emitting Diode (LED) display or another display technology as known.

The I/O unit 1512 can include at least one of a mouse, a keyboard, a touch screen, a thumbwheel, a track-pad, a track-ball, a card-reader, voice recognition software and the like again depending on the particular implementation of the server 1500. In some cases, some of these components can be integrated with one another.

The power unit 1516 can be any suitable power source that provides power to the server 1500 such as a power adaptor or a rechargeable battery pack depending on the implementation of the server 1500 as is known by those skilled in the art.

The memory unit 1510 comprises software code for implementing an operating system 1520, programs 1522, a test indication Application Programming Interface (API) 1524, a test reading API 1526, a facial recognition unit 1528, a 3rd party identification unit 1530, and a database 1532.

The memory unit 1510 can include RAM, ROM, one or more hard drives, one or more flash drives or some other suitable data storage elements such as disk drives, etc. The memory unit 1510 is used to store an operating system 1520 and programs 1522 as is commonly known by those skilled in the art. For instance, the operating system 1520 provides various basic operational processes for the server 1500. For example, the operating system 1520 may be a server operating system such as Ubuntu Linux, CentOS, or a Windows based operating system including Windows, or another operating system.

The programs 1522 include various user programs so that a user can interact with the server 1500 to perform various functions such as, but not limited to, receiving test indications, sending test indications, performing facial recognition, associating test indications with $3^{rd}$ party identification numbers, and storing data related to these items in a database.

The test indication API 1524 may receive test indications from a test device via communication unit 1504 from a network. These test indications may further include data associated with the test performed by a subject, such as particle detector data and spectrometer data. The test indications may further include information associated with the subject being tested, such as personal information, a facial image or a facial identifier taken by the test device, and other 3$^{rd}$ party identification information such as identification numbers.

In response to receiving the test indication and associated data, the test indication API 1524 may store the indication and associated data in a database 1532.

In one embodiment, the test device transmits the particle detector data and the spectroscope data to the test indication API 1524, and the test indication API 1524 performs the methods of FIGS. 10 and 11, in order to perform the test sufficiency determination and test indication determinations for the test device.

Figure 16:
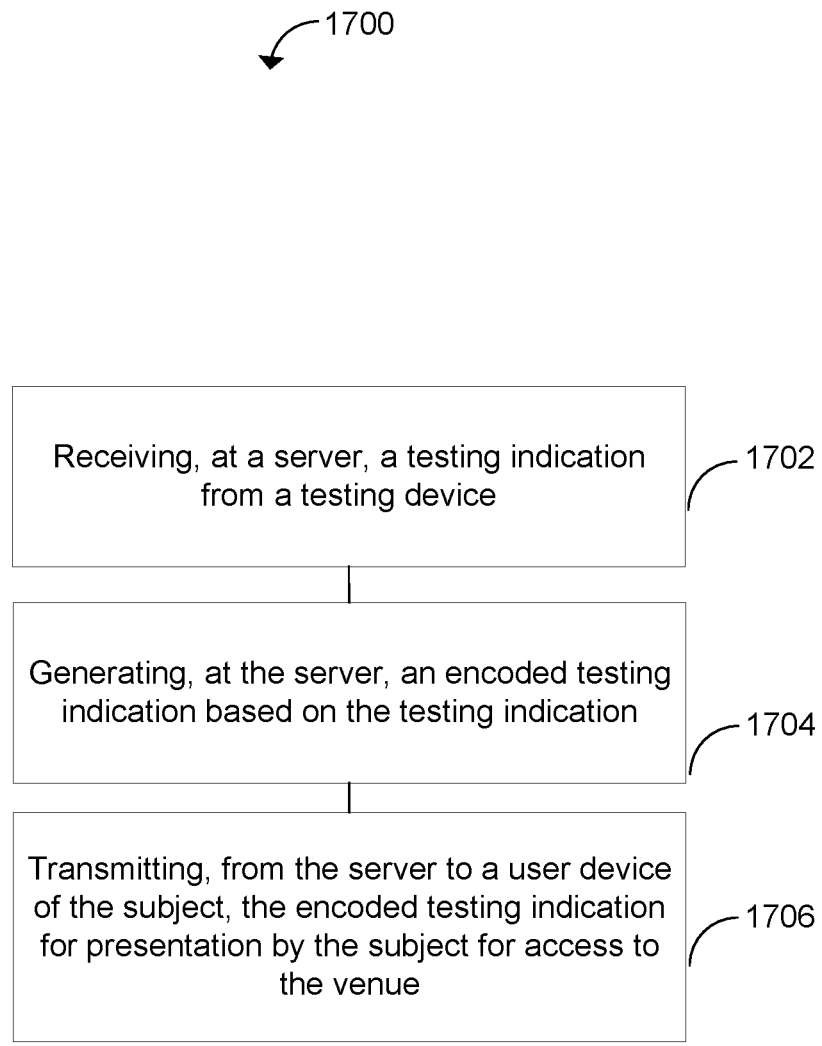
FIG. 16 is a process flow for generating a test pass allowing access to a venue.

In one embodiment, the server 1500 may receive the test indication and associated information from the test device, may generate the test pass based on the test indication and associated information, and may respond to the mobile device of the subject and/or the test device and transmit the test pass in response (see FIG. 16). The communication between the mobile device of the subject, the test device, and the server may be encrypted.

The test reading API 1526 may receive requests from venues to verify a test pass. The subject may present a test pass at a venue, and the venue may read it using, for example, a barcode scanner or a smartphone connected camera. The test pass may be read by the reader at the venue, and a request made to server 1500 in order to confirm that the test pass is authentic, and that the subject has a negative test indication.

Facial Recognition

The facial recognition unit 1528 may provide facial recognition services to venues, such that the status of a test pass for a subject can be validated based on a facial image on the subject. The server 1500 may also receive a facial image recorded by the venue of the subject, and may validate the facial image against a stored facial image in the database using facial recognition unit 1528, which may be taken when a subject takes a test using a testing device 1410. In order to preserve subject privacy, the facial image may be transformed into a facial identifier using a one-way mathematical transformation, and the recorded facial identifier at the venue may be checked against a stored facial identifier in the database 1532.

Referring back to FIGS. 12 and 14, a proximity detector at a testing device 1410 may take a facial image of the subject when testing is performed. The test indication, along with subject information may be transmitted from the test device 1410 to the server 1406 via network 1404 and stored in database 1408.

The server 1406 or the testing device 1410 may determine a facial identifier from the facial image, and may associate the testing indication with the facial identifier. The facial identifier may be used by a facial recognition algorithm to associate the testing indication with the subject's face.

In an alternate embodiment, a one-way mathematical function may be used on the facial image or the facial identifier by the testing device 1410 so that personal information is not stored in the database, i.e. the data may be anonymized and may only associate the test indication with the facial identifier.

3$^{rd}$ Party Identification

Referring again to FIG. 15, the 3$^{rd}$ party identification unit 1530 which provides for test passes to be associated with 3$^{rd}$ party identification including loyalty cards, government issued identification cards, and other identification information.

The 3$^{rd}$ party identification information may be received from the test device, and may include, for example, a 3$^{rd}$ party identifier, a 3$^{rd}$ party identification number (for example a driver's license number), or an image of the identification card.

The test indication API 1524 may generate a test pass, and when doing so may encode information associating the pass with a 3$^{rd}$ party identification card. When the test pass is presented, the subject may be required to present the identification along with the pass.

The 3$^{rd}$ party identification unit 1530 may associate received data from a subject with the 3$^{rd}$ party identification information stored in database 1532.

Test Scheduling

The scheduling unit 1531 may allow a subject to book a time slot at a testing device using a web interface or a downloadable application on their mobile device. This may allow, for example, a subject to book a time for testing prior to entry to a building, event, plane, or cruise ship. In another example, testing may be conducted on a cruise ship by a subject who may schedule a testing time slot, e.g., half an hour prior to their dinner reservation or disembarking for a tour.

The scheduling unit 1531 may further allow the test device to be physically located away from the venue. This may help to minimize lineups at entry point to the venue as subjects could be tested in advance and seek entry using a test pass as described herein. In this way, government mandated physical distancing requirements may be maintained by subjects during testing.

The database 1532 may be a Structured Query Language (SQL) such as PostgreSQL or MySQL or a not only SQL (NoSQL) database such as MongoDB, or Graph Databases etc.

Reference is next made to FIG. 16, there is shown process flow 1700 for generating a test pass allowing access to a venue.

At 1702, receiving, at a server, a testing indication from a testing device.

At 1704, generating, at the server, an encoded testing indication based on the testing indication.

At 1706, transmitting, from the server to a user device of the subject, the encoded testing indication for presentation by the subject for access to the venue.

Optionally, encoding a time identifier and the testing indication in the encoded testing indication.

Optionally, storing, at a database, the time identifier, the testing indication, and the encoded testing indication.

Optionally, receiving, at the server from the test device, a geographic identifier of the test device; and wherein the generating the encoded testing indication further comprises encoding the geographic identifier and the testing indication in the encoded testing indication.

Optionally, storing, at a database, the geographic identifier, the testing indication, and the encoded testing indication.

Optionally, receiving, at the server from the test device, a facial image of the subject; determining, at the server, a facial identifier based on the facial image; and wherein the generating the encoded testing indication further comprises encoding the facial identifier and the testing indication in the encoded testing indication.

Optionally, storing, at a database, the facial identifier, the testing indication, and the encoded testing indication.

Optionally, receiving, at the server from the test device, a third-party identification number of the subject; wherein the generating the encoded testing indication further comprises encoding the third-party identification number and the testing indication in the encoded testing indication.

Optionally, storing, at a database, the third-party identification number, the testing indication, and the encoded testing indication.

Optionally, receiving, at the server, a request from the subject for a testing time slot; and transmitting, from the server to the user device, a confirmation of the testing time slot.

Optionally, storing, at a database, the geographic identifier, the testing indication, and the encoded testing indication.

Optionally, receiving, at the server from the test device, a facial image of the subject; determining, at the server, a facial identifier based on the facial image; and wherein the generating the encoded testing indication further comprises encoding the facial identifier and the testing indication in the encoded testing indication.

Optionally, storing, at a database, the facial identifier, the testing indication, and the encoded testing indication.

Optionally, receiving, at the server from the test device, a third-party identification number of the subject; wherein the generating the encoded testing indication further comprises encoding the third-party identification number and the testing indication in the encoded testing indication.

Optionally, storing, at a database, the third-party identification number, the testing indication, and the encoded testing indication.

Optionally, receiving, at the server, a request from the subject for a testing time slot; and transmitting, from the server to the user device, a confirmation of the testing time slot.

Optionally, the encoded testing indication is one of the group of a barcode, a Quick Response (QR) code, and a Radio-Frequency Identifier (RFID) code.

Figure 17:
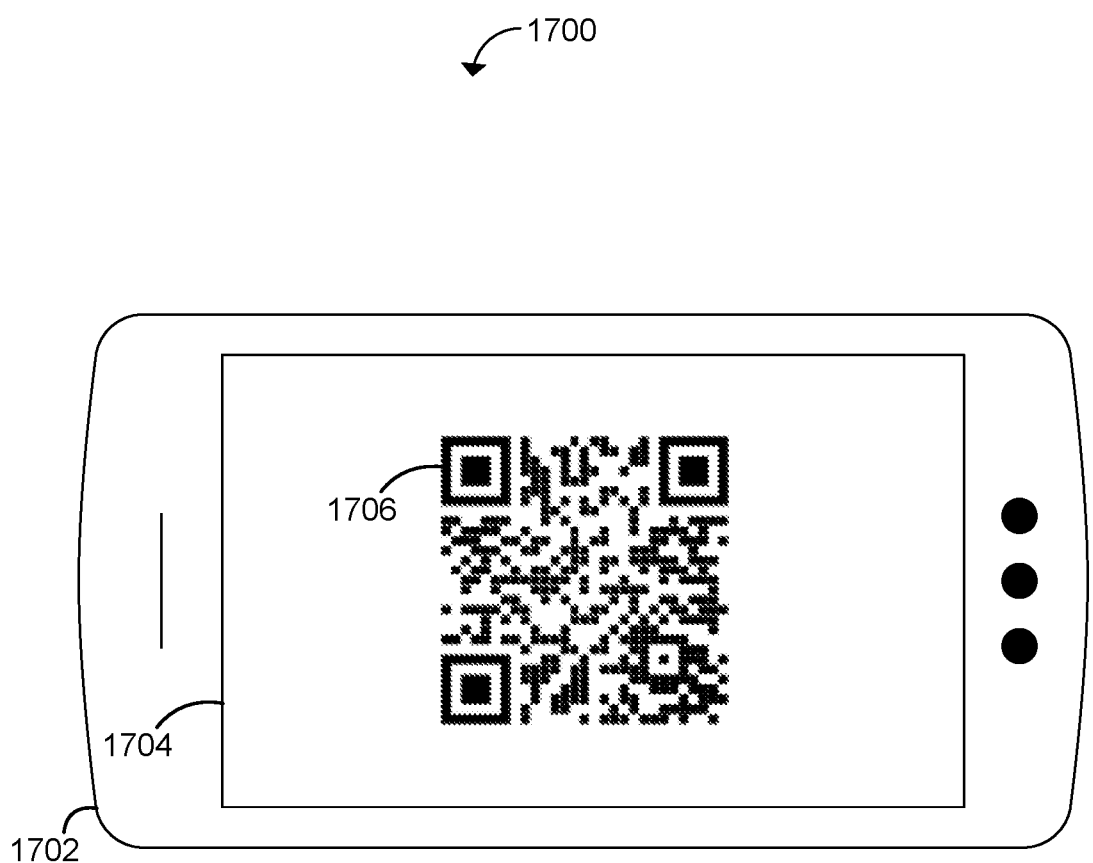
FIG. 17 is a user interface for allowing access to a venue.

Reference is next made to FIG. 17, showing a user interface 1700 for allowing access to a venue.

The user interface 1700 is displayed on mobile device 1702 (for example, mobile device 1412 in FIG. 14). The display device 1704 of mobile device 1702 may display the test pass 1706, including encoded test indication information. The test pass 1706 may include a barcode or other machine readable design (in the example shown, a QR code).

The test pass 1706 displayed on the user device 1702 may be received by a subject after performing testing at a testing device. The test pass 1706 may be displayed on the user device 1702 and presented at a venue in order to gain entry or access to the venue.

The present invention has been described here by way of example only. Various modification and variations may be made to these exemplary embodiments without departing from the spirit and scope of the invention, which is limited only by the appended claims. It will be appreciated that a test device may include any one or more of the features set out herein and a method of obtaining and making available a test pass may use one or more of the steps set out herein.

I claim:

1. A method for non-invasive respiratory testing of a subject for presence of a biological agent, the method comprising:
   receiving, at an opening of a chamber, a breath sample from the subject;
   receiving, at a processor, first spectrum data of the breath sample from a first spectrometer;
   receiving, at the processor, second spectrum data of the breath sample from a second spectrometer;
   receiving, at the processor, third spectrum data of the breath sample from a third spectrometer;
   receiving, at a processor, particle detector data from a particle detector;
   determining, at the processor, a testing indication based on the first spectrum data, the second spectrum data, and the third spectrum data, the testing indication being positive if at least two of the first spectrum data, the second spectrum data, and the third spectrum data indicate a positive test result showing the presence of the biological agent and if the particle detector data indicates a sufficient sample has been obtained from the subject; and
   outputting, at a display device, the testing indication.

2. The method of claim 1, wherein the determining, at the processor, a testing indication further comprises:
   receiving, at the processor, fourth spectrum data from a fourth spectrometer;
   receiving, at the processor, fifth spectrum data from a fifth spectrometer;
   determining a fourth spectrometer indication based on the fourth spectrum data;
   determining a fifth spectrometer indication based on the fifth spectrum data;
   determining the testing indication by performing an arbitration of the first spectrometer indication, the second spectrometer indication, the third spectrometer indication, the fourth spectrometer indication, and the fifth spectrometer indication.

3. The method of claim 2), wherein the determining, at the processor, a testing indication further comprises:
   receiving, at the processor, sixth spectrum data from a sixth spectrometer;
   receiving, at the processor, seventh spectrum data from a seventh spectrometer;
   determining a sixth spectrometer indication based on the sixth spectrum data;
   determining a seventh spectrometer indication based on the seventh spectrum data;
   determining the testing indication by performing an arbitration of the first spectrometer indication, the second spectrometer indication, the third spectrometer indication, the fourth spectrometer indication, the fifth spectrometer indication, the sixth spectrometer indication, and the seventh spectrometer indication.

4. A system for non-invasive respiratory testing of a subject for presence of a biological agent, the system comprising:
   a chamber, the chamber comprising:
      an opening for receiving a breath sample from the subject,
      a first spectrometer for collecting first spectrum data of the breath sample,
      a second spectrometer for collecting second spectrum data of the breath sample, and
      a third spectrometer for collecting third spectrum data of the breath sample;

a particle detector;
a memory;
a display device for displaying a testing indication; and
a processor in communication with the first spectrometer, the second spectrometer, the third spectrometer, the memory, the particle detector, and the display device, the processor configured to:
  receive the first spectrum data of the breath sample from the first spectrometer;
  receive the second spectrum data of the breath sample from the second spectrometer;
  receive the third spectrum data of the breath sample from the third spectrometer;
  receive particle detector data from the particle detector;
  determine the testing indication based on the first spectrum data, the second spectrum data, and the third spectrum data, the testing indication being positive if at least two of the first spectrum data, the second spectrum data, and the third spectrum data indicate a positive test result showing the presence of the biological agent and if the particle detector data indicates a sufficient sample has been obtained from the subject; and
  output, at the display device, the testing indication.

5. The system of claim 4, wherein the testing indication is further determined by performing sensor fusion on the first spectrum data, the second spectrum data, and the third spectrum data.

6. The system of claim 5, wherein the processor is configured to determine the test indication by:

determining a first spectrometer indication based on the first spectrum data;
determining a second spectrometer indication based on the second spectrum data;
determining a third spectrometer indication based on the third spectrum data;
determining the testing indication by performing an arbitration of the first spectrometer indication, the second spectrometer indication, and the third spectrometer indication.

7. The system of claim 6, further comprising:
a fourth spectrometer for collecting fourth spectrum data of the breath sample and a fifth spectrometer for collecting fifth spectrum data of the breath sample;
wherein the processor is further configured to determine the test indication by:
  receiving fourth spectrum data from the fourth spectrometer;
  receiving fifth spectrum data from the fifth spectrometer;
  determining a fourth spectrometer indication based on the fourth spectrum data;
  determining a fifth spectrometer indication based on the fifth spectrum data;
  determining the testing indication by performing an arbitration of the first spectrometer indication, the second spectrometer indication, the third spectrometer indication, the fourth spectrometer indication, and the fifth spectrometer indication.

* * * * *